(12) United States Patent
Goble et al.

(10) Patent No.: US 6,306,134 B1
(45) Date of Patent: *Oct. 23, 2001

(54) ELECTROSURGICAL GENERATOR AND SYSTEM

(75) Inventors: Nigel Mark Goble, Castleton, Nr. Cardiff; Colin Charles Owen Goble, South Glamorgan, both of (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/173,728

(22) Filed: Oct. 16, 1998

Related U.S. Application Data

(62) Division of application No. 08/642,121, filed on May 2, 1996.

(30) Foreign Application Priority Data

| Jun. 23, 1995 | (GB) | 9512888 |
| Jun. 23, 1995 | (GB) | 9512889 |
| Dec. 29, 1995 | (GB) | 9526627 |
| Mar. 6, 1996 | (GB) | 9604770 |

(51) Int. Cl.⁷ .................................................. A61B 17/32
(52) U.S. Cl. .................................. 606/42; 606/34; 606/41
(58) Field of Search ................................ 606/40–52, 34

(56) References Cited

U.S. PATENT DOCUMENTS

| Re. 33,925 | 5/1992 | Bales et al. . |
| 164,184 | 6/1875 | Kidder . |
| 1,366,756 | 1/1921 | Wappler . |
| 1,735,271 | 11/1929 | Groff . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |

(List continued on next page.)

FOREIGN PATENT DOCUMENTS

| 243478 | 7/1946 | (CH) . |
| 222207 | 5/1985 | (DD) . |

(List continued on next page.)

OTHER PUBLICATIONS

Cook, Albert M. & John C. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

Wyeth, G.A., *Electrosurgical Unit*, pp. 1180–1202.

Everest Medical Technologies, Inc., "Everest Bipolar Laproscopic Cholecystectomy," Transcript of Lecture by Dr. Olsen, Oct. 7, 1991.

(List continued on next page.)

*Primary Examiner*—David M. Shay
(74) *Attorney, Agent, or Firm*—Nixon & Vanderhye P.C.

(57) ABSTRACT

An electrosurgical system including an electrode assembly having two electrodes for use immersed in an electrically conductive fluid has a generator with control circuitry for rapidly reducing the delivered radio frequency output power by at least 50% within at most a few cycles of the peak radio frequency output voltage reaching a predetermined threshold limit. In this way, tissue coagulation can be performed in, for example, saline without significant steam generation. The same peak voltage limitation technique is used in a tissue vaporization or cutting mode to limit the size of the steam pocket at the electrodes and to avoid electrode burning.

4 Claims, 7 Drawing Sheets

U.S. PATENT DOCUMENTS

| | | |
|---|---|---|
| 1,952,617 | 3/1934 | Wappler . |
| 1,983,669 | 12/1934 | Kimble . |
| 2,050,904 | 8/1936 | Trice . |
| 2,056,377 | 10/1936 | Wappler . |
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |
| 3,707,149 | 12/1972 | Hao et al. . |
| 3,801,766 | 4/1974 | Morrison, Jr. . |
| 3,815,604 | 6/1974 | O'Malley et al. . |
| 3,845,771 | 11/1974 | Vise . |
| 3,847,153 | 11/1974 | Weissman . |
| 3,870,047 | 3/1975 | Gonser . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. . |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers et al. . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels . |
| 5,013,312 | 5/1991 | Parins et al. . |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker et al. . |
| 5,071,418 | 12/1991 | Rosenbaum . |
| 5,080,660 | 1/1992 | Buelna . |

| | | | | | |
|---|---|---|---|---|---|
| 5,083,565 | 1/1992 | Parins . | 5,422,567 | 6/1995 | Matsunaga . |
| 5,085,659 | 2/1992 | Rydell . | 5,423,808 | 6/1995 | Edwards et al. . |
| 5,088,997 | 2/1992 | Delahuerga et al. . | 5,423,809 | 6/1995 | Klicek . |
| 5,098,431 | 3/1992 | Rydell . | 5,423,810 | 6/1995 | Goble et al. . |
| 5,099,840 | 3/1992 | Goble et al. . | 5,423,811 | 6/1995 | Imran et al. . |
| 5,108,391 | 4/1992 | Flachenecker et al. . | 5,431,649 | 7/1995 | Mulier et al. . |
| 5,108,407 | 4/1992 | Geremia et al. . | 5,437,662 | 8/1995 | Nardella . |
| 5,117,978 | 6/1992 | Blumenfeld et al. . | 5,438,302 | 8/1995 | Goble . |
| 5,133,365 | 7/1992 | Heil, Jr. et al. . | 5,441,499 | 8/1995 | Fritzsch . |
| 5,158,561 | 10/1992 | Rydell et al. . | 5,443,470 | 8/1995 | Stern et al. . |
| 5,167,658 | 12/1992 | Ensslin . | 5,454,809 | 10/1995 | Janssen . |
| 5,167,659 | 12/1992 | Ohtomo et al. . | 5,462,521 | 10/1995 | Brucker et al. . |
| 5,171,255 | 12/1992 | Rydell . | 5,472,441 | 12/1995 | Edwards et al. . |
| 5,171,311 | 12/1992 | Rydell et al. . | 5,472,443 | 12/1995 | Cordis et al. . |
| 5,178,620 | 1/1993 | Eggers et al. . | 5,480,397 | 1/1996 | Eggers et al. . |
| 5,190,517 | 3/1993 | Zieve et al. . | 5,480,398 | 1/1996 | Eggers et al. . |
| 5,195,959 | 3/1993 | Smith . | 5,496,312 | 3/1996 | Klicek . |
| 5,196,007 | 3/1993 | Ellman et al. . | 5,496,314 | 3/1996 | Eggers . |
| 5,197,963 | 3/1993 | Parins . | 5,505,728 | 4/1996 | Ellman et al. . |
| 5,201,743 | 4/1993 | Haber et al. . | 5,505,730 | 4/1996 | Edwards . |
| 5,207,675 | 5/1993 | Canady . | 5,507,743 | 4/1996 | Edwards et al. . |
| 5,217,457 | 6/1993 | Delahuerga et al. . | 5,514,129 | 5/1996 | Smith . |
| 5,217,458 | 6/1993 | Parins . | 5,514,130 | 5/1996 | Baker . |
| 5,217,459 | 6/1993 | Kamerling . | 5,514,131 | 5/1996 | Edwards et al. . |
| 5,221,281 | 6/1993 | Klicek . | 5,520,684 | 5/1996 | Imran . |
| 5,244,462 | 9/1993 | Delahuerga et al. . | 5,520,685 | 5/1996 | Wojciechowicz . |
| 5,249,585 | 10/1993 | Turner et al. . | 5,522,815 | 6/1996 | Durgin, Jr. et al. . |
| 5,250,047 | 10/1993 | Rydell . | 5,531,744 | 7/1996 | Nardella et al. . |
| 5,258,006 | 11/1993 | Rydell et al. . | 5,536,267 | 7/1996 | Edwards et al. . |
| 5,259,395 | 11/1993 | Li . | 5,540,680 | 7/1996 | Guglielmi et al. . |
| 5,261,906 | 11/1993 | Pennino et al. . | 5,540,681 | 7/1996 | Strul et al. . |
| 5,267,994 | 12/1993 | Gentelia et al. . | 5,540,682 | 7/1996 | Gardner et al. . |
| 5,267,997 | 12/1993 | Farin et al. . | 5,540,683 | 7/1996 | Ichikawa et al. . |
| 5,277,201 | 1/1994 | Stern . | 5,540,684 | 7/1996 | Hassler, Jr. . |
| 5,277,696 | 1/1994 | Hagen . | 5,540,685 | 7/1996 | Parins et al. . |
| 5,281,213 | 1/1994 | Milder et al. . | 5,542,916 | 8/1996 | Hirsch et al. . |
| 5,281,216 | 1/1994 | Klicek . | 5,542,945 | 8/1996 | Fritzsch . |
| 5,282,799 | 2/1994 | Rydell . | 5,545,161 | 8/1996 | Imran . |
| 5,282,845 | 2/1994 | Bush et al. . | 5,545,193 | 8/1996 | Fleischman et al. . |
| 5,290,282 | 3/1994 | Casscells . | 5,549,605 | 8/1996 | Hahnen . |
| 5,290,283 | 3/1994 | Suda . | 5,554,172 | 9/1996 | Horner et al. . |
| 5,300,068 | 4/1994 | Rosar et al. . | 5,555,618 | 9/1996 | Winkler . |
| 5,300,069 | 4/1994 | Hunsberger et al. . | 5,556,396 | 9/1996 | Cohen et al. . |
| 5,300,070 | 4/1994 | Gentelia et al. . | 5,556,397 | 9/1996 | Long et al. . |
| 5,304,214 | 4/1994 | DeFord et al. . | 5,558,671 | 9/1996 | Yates . |
| 5,306,238 | 4/1994 | Fleenor . | 5,562,720 | 10/1996 | Stern et al. . |
| 5,317,155 | 5/1994 | King . | 5,569,164 | 10/1996 | Lurz . |
| 5,318,563 | 6/1994 | Malis et al. . | 5,569,242 | 10/1996 | Lax et al. . |
| 5,320,627 | 6/1994 | Sorensen et al. . | 5,569,244 | 10/1996 | Hahnen . |
| 5,330,470 | 7/1994 | Hagen . | 5,569,245 | 10/1996 | Guglielmi et al. . |
| 5,330,471 | 7/1994 | Eggers . | 5,575,789 | 11/1996 | Bell et al. . |
| 5,334,193 | 8/1994 | Nardella . | 5,578,007 | 11/1996 | Imran . |
| 5,334,198 | 8/1994 | Hart et al. . | 5,582,609 | 12/1996 | Swanson et al. . |
| 5,336,222 | 8/1994 | Durgin, Jr. et al. . | 5,582,610 | 12/1996 | Grossi et al. . |
| 5,342,357 | 8/1994 | Nardella . | 5,584,830 | 12/1996 | Ladd et al. . |
| 5,342,391 | 8/1994 | Foshee et al. . | 5,591,141 | 1/1997 | Nettekoven . |
| 5,344,428 | 9/1994 | Griffiths . | 5,599,344 | 2/1997 | Paterson . |
| 5,352,222 | 10/1994 | Rydell . | 5,599,345 | 2/1997 | Edwards et al. . |
| 5,354,296 | 10/1994 | Turkel . | 5,599,346 | 2/1997 | Edwards et al. . |
| 5,370,645 | 12/1994 | Klicek et al. . | 5,599,347 | 2/1997 | Hart et al. . |
| 5,370,675 | 12/1994 | Edwards et al. . | 5,599,348 | 2/1997 | Gentelia et al. . |
| 5,372,596 | 12/1994 | Klicek et al. . | 5,599,349 | 2/1997 | D'Amelio . |
| 5,382,247 | 1/1995 | Cimino et al. . | 5,603,711 | 2/1997 | Parins et al. . |
| 5,383,874 | 1/1995 | Jackson et al. . | 5,603,712 | 2/1997 | Koranda et al. . |
| 5,383,876 | 1/1995 | Nardella . | 5,607,422 | 3/1997 | Smeets et al. . |
| 5,383,917 | 1/1995 | Desai et al. . | 5,609,151 | 3/1997 | Mulier et al. . |
| 5,383,923 | 1/1995 | Webster, Jr. . | 5,609,573 | 3/1997 | Sandock . |
| 5,395,363 | 3/1995 | Billings et al. . | 5,611,798 | 3/1997 | Eggers . |
| 5,395,368 | 3/1995 | Ellman et al. . | 5,620,481 | 4/1997 | Desai et al. . |
| 5,403,311 | 4/1995 | Abele et al. . | 5,624,439 | 4/1997 | Edwards et al. . |
| 5,419,767 | 5/1995 | Eggers et al. . | 5,626,560 | 5/1997 | Soring . |

| | | | | | |
|---|---|---|---|---|---|
| 5,626,575 | 5/1997 | Crenner . | 0 316469 A1 | 5/1989 | (EP) . |
| 5,626,576 | 5/1997 | Janssen . | 0 325456 A2 | 7/1989 | (EP) . |
| 5,626,578 | 5/1997 | Tihon . | 0 332308 A2 | 9/1989 | (EP) . |
| 5,628,745 | 5/1997 | Bek . | 0 373670 A2 | 6/1990 | (EP) . |
| 5,628,771 | 5/1997 | Mizukawa et al. . | 0 392837 A3 | 10/1990 | (EP) . |
| 5,630,426 | 5/1997 | Eggers et al. . | 0 407057 A1 | 1/1991 | (EP) . |
| 5,633,578 | 5/1997 | Eggers et al. . | 0 412426 A2 | 2/1991 | (EP) . |
| 5,634,924 | 6/1997 | Turkel et al. . | 0 437377 A1 | 7/1991 | (EP) . |
| 5,672,174 | 9/1997 | Gough et al. . | 0 448798 A1 | 10/1991 | (EP) . |
| 5,683,366 | 11/1997 | Eggers et al. . | 0 499491 A2 | 8/1992 | (EP) . |
| 5,693,045 | 12/1997 | Eggers . | 0 507622 A1 | 10/1992 | (EP) . |
| 5,697,281 | 12/1997 | Eggers et al. . | 0 509670 A2 | 10/1992 | (EP) . |
| 5,697,536 | 12/1997 | Eggers et al. . | 0 517243 A1 | 12/1992 | (EP) . |
| 5,697,882 | 12/1997 | Eggers et al. . | 0 518230 A1 | 12/1992 | (EP) . |
| 5,697,909 | 12/1997 | Eggers et al. . | 0 530400 A1 | 3/1993 | (EP) . |
| 5,700,262 | 12/1997 | Acosta et al. . | 0 536440 A1 | 4/1993 | (EP) . |
| 5,725,524 | 3/1998 | Mulier et al. . | 0 558316 A1 | 9/1993 | (EP) . |
| 5,735,846 | 4/1998 | Panescu et al. . | 0 558318 A1 | 9/1993 | (EP) . |
| 5,766,153 | 6/1998 | Eggers et al. . | 0 647435 A1 | 4/1995 | (EP) . |
| 5,810,764 | 9/1998 | Eggers et al. . | 0 653192 A2 | 5/1995 | (EP) . |
| 5,833,689 | 11/1998 | Long . | 0 667680 A1 | 8/1995 | (EP) . |
| 5,843,019 | 12/1998 | Eggers et al. . | 0 674909 A2 | 10/1995 | (EP) . |
| 5,860,951 | 1/1999 | Eggers et al. . | 0 684015 A1 | 11/1995 | (EP) . |
| 5,871,469 | 2/1999 | Eggers et al. . | 0 688536 A1 | 12/1995 | (EP) . |
| 5,873,855 | 2/1999 | Eggers et al. . | 0 692224 A2 | 1/1996 | (EP) . |
| 5,888,198 | 3/1999 | Eggers et al. . | 0 694290 A1 | 1/1996 | (EP) . |
| 5,891,095 | 4/1999 | Eggers et al. . | 0 697199 A1 | 2/1996 | (EP) . |
| 5,902,272 | 5/1999 | Eggers et al. . | 0 709065 A1 | 5/1996 | (EP) . |
| 5,941,876 | 8/1999 | Nardella et al. . | 57862 | 9/1953 | (FR) . |

FOREIGN PATENT DOCUMENTS

| | | | | | |
|---|---|---|---|---|---|
| 1215305 | 4/1960 | (FR) . | | | |
| 1454773 | 10/1966 | (FR) . | | | |
| 651428 | 9/1937 | (DE) . | 2313949 | 1/1977 | (FR) . |
| 1007960 | 5/1957 | (DE) . | 2443829 | 7/1980 | (FR) . |
| 2222820 | 11/1973 | (DE) . | 2501034 | 9/1982 | (FR) . |
| 2457900 B1 | 5/1976 | (DE) . | 1361497 | 7/1974 | (GB) . |
| 2930982 A1 | 2/1981 | (DE) . | 2037167 | 7/1980 | (GB) . |
| 3209444 A1 | 10/1982 | (DE) . | 1583397 | 1/1981 | (GB) . |
| 3215832A1 | 11/1982 | (DE) . | 2133290 | 7/1984 | (GB) . |
| 3119735 A1 | 1/1983 | (DE) . | 2145932 | 4/1985 | (GB) . |
| 3245570 C2 | 6/1984 | (DE) . | 2161081 | 1/1986 | (GB) . |
| 3423356 A1 | 1/1986 | (DE) . | 2164473 | 3/1986 | (GB) . |
| 3427517 A1 | 1/1986 | (DE) . | 2177309 | 1/1987 | (GB) . |
| 3511107 A1 | 10/1986 | (DE) . | 2179861 | 3/1987 | (GB) . |
| 3623688 A1 | 1/1987 | (DE) . | 2213381 A | 8/1989 | (GB) . |
| 3530335 C2 | 3/1987 | (DE) . | 2214430 | 9/1989 | (GB) . |
| 3707820 A1 | 9/1987 | (DE) . | 62211060 | 9/1987 | (JP) . |
| 3622337 C2 | 1/1988 | (DE) . | 644491 | 1/1979 | (RU) . |
| 3642077 C2 | 6/1988 | (DE) . | WO 81/03271 | 11/1981 | (WO) . |
| 3708801 C2 | 9/1988 | (DE) . | WO 82/00084 | 1/1982 | (WO) . |
| 3824913 A1 | 2/1990 | (DE) . | WO 82/02488 | 8/1982 | (WO) . |
| 3838840 C2 | 5/1990 | (DE) . | WO 84/03829 | 10/1984 | (WO) . |
| 3930451 A1 | 3/1991 | (DE) . | WO 88/01851 | 3/1988 | (WO) . |
| 4108269 C2 | 6/1992 | (DE) . | WO 90/03152 | 4/1990 | (WO) . |
| 4103972 C2 | 8/1992 | (DE) . | WO 93/08756 | 5/1993 | (WO) . |
| 4126608 A1 | 2/1993 | (DE) . | WO 93/13718 | 7/1993 | (WO) . |
| 4139029 C2 | 6/1993 | (DE) . | WO 93/13816 | 7/1993 | (WO) . |
| 4217999 A1 | 12/1993 | (DE) . | WO 93/16650 | 9/1993 | (WO) . |
| 4237321 A1 | 5/1994 | (DE) . | WO 93/19681 | 10/1993 | (WO) . |
| 4323585 | 1/1995 | (DE) . | WO 93/19682 | 10/1993 | (WO) . |
| 4339049 A1 | 5/1995 | (DE) . | WO 93/20747 | 10/1993 | (WO) . |
| 4425015 A1 | 1/1996 | (DE) . | WO 93/20877 | 10/1993 | (WO) . |
| 19530004 A1 | 3/1996 | (DE) . | WO 94/04220 | 3/1994 | (WO) . |
| 4429478 C1 | 3/1996 | (DE) . | WO 94/06510 | 3/1994 | (WO) . |
| 0 013605 A1 | 7/1980 | (EP) . | WO 94/10921 | 5/1994 | (WO) . |
| 0 049633 A1 | 4/1982 | (EP) . | WO 94/10924 | 5/1994 | (WO) . |
| 0 067680 A1 | 12/1982 | (EP) . | WO 94/10925 | 5/1994 | (WO) . |
| 0 136855 A2 | 4/1985 | (EP) . | WO 94/23659 | 10/1994 | (WO) . |
| 0 219568 A1 | 12/1985 | (EP) . | WO 94/26228 | 11/1994 | (WO) . |
| 0 205851 A1 | 12/1986 | (EP) . | WO 94/28809 | 12/1994 | (WO) . |
| 0 280798A 1 | 9/1988 | (EP) . | WO 95/02369 | 1/1995 | (WO) . |
| 0 310431 A2 | 4/1989 | (EP) . | WO 95/05781 | 3/1995 | (WO) . |

| | | |
|---|---|---|
| WO 95/09576 | 4/1995 | (WO) . |
| WO 95/09577 | 4/1995 | (WO) . |
| WO 95/10320 | 4/1995 | (WO) . |
| WO 95/10321 | 4/1995 | (WO) . |
| WO 95/17855 | 7/1995 | (WO) . |
| WO 95/18575 | 7/1995 | (WO) . |
| WO 95/19733 | 7/1995 | (WO) . |
| WO 95/20360 | 8/1995 | (WO) . |
| WO 95/23558 | 9/1995 | (WO) . |
| WO 95/24160 | 9/1995 | (WO) . |
| WO 95/25472 | 9/1995 | (WO) . |
| WO 95/26686 | 10/1995 | (WO) . |
| WO 95/30377 | 11/1995 | (WO) . |
| WO 95/31144 | 11/1995 | (WO) . |
| WO 96/00036 | 1/1996 | (WO) . |
| WO 96/00039 | 1/1996 | (WO) . |
| WO 96/00040 | 1/1996 | (WO) . |
| WO 96/00042 | 1/1996 | (WO) . |
| WO 96/00043 | 1/1996 | (WO) . |
| WO 96/00528 | 1/1996 | (WO) . |
| WO 96/04859 | 2/1996 | (WO) . |
| WO 96/07360 | 3/1996 | (WO) . |
| WO 96/09010 | 3/1996 | (WO) . |
| WO 96/10367 | 4/1996 | (WO) . |

OTHER PUBLICATIONS

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995 10 pages.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–672, 674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., A Bipolar Electrosurgical TURP Loop, Abstract of Paper P14–11, 7th World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/ Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis, J. et al., "Vaporization of Atherosclerotic Plaques by Spark Erosion," Journal of American College of Cardiology, 1985, pp. 1382–6.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J.,. "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., Electrosurgery in Operative Endoscopy, Blackwell Science Ltd., London, 1995, pp. 87–93, 155–163.

Farin, G., "Pneumatically Controlled Bipolar Cutting Instrument," End. Surg., 1993, pp. 1–3 No figures.

Muller, W., "The Advantages of Laparoscopic Assisted Bipolar High–Frequency Surgery," End. Surg., 1993, pp. 1–6.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994 one page.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," Reprint from *Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases*, CRC Press, New York, 1998, p. 93 (commentary on Honig, William M., "The Mechanism of Cutting in Electrosurgery," IEEE Transactions on Biomedical Engineering, Jan. 1975, pp. 93 (one page).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996 p. 6–1.

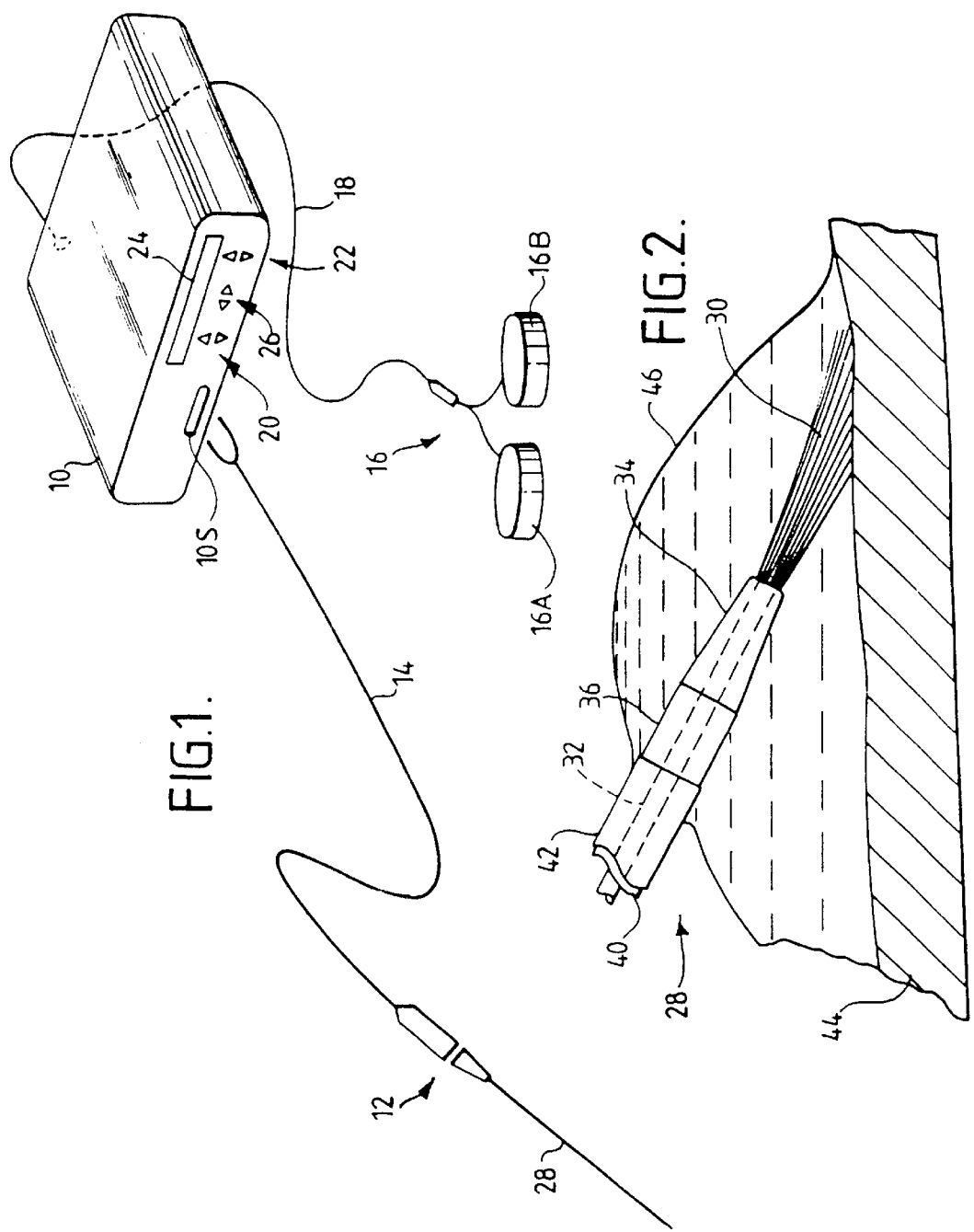

ELECTROSURGICAL GENERATOR AND SYSTEM

This is a Divisional of application Ser. No. 08/642,121, filed May 2, 1996, now pending.

FIELD OF THE INVENTION

This invention relates to an electrosurgical generator for delivering an electrosurgical current particularly but not exclusively in intracavitary endoscopic electrosurgery. The invention also relates to an electrosurgical system comprising the combination of a generator and an electrode assembly. The term "intracavitary" is used in this specification to denote electrosurgery in which living tissue is treated by least invasive surgical access to a body cavity. This may involve "underwater electrosurgery", a term denoting that the surgery is performed using an electrosurgical instrument with a treatment electrode or electrodes immersed in liquid at the operation site. The invention has particular application in the fields of uroloagy, hysteroscopy and arthroscopy.

BACKGROUND OF THE INVENTION

Intracavitary endoscopic electrosurgery is useful for treating tissue in anatomical or surgically created cavities of the body which can be accessed by methods involving minimal trauma to the patient, be this through a natural body passage or one created artificially. The cavity is distended to provide space for gaining access to the operation site to improve visualisation and to allow for manipulation of instruments. In low volume body cavities, particularly where it is desirable to distend the cavity under higher pressure, liquid rather than gas is more commonly used due to better optical characteristics and because it washes blood away from the operative site. Conventionally, a non-electrolyte solution such as glycine is used as the fluid distension medium when electrosurgery is being used, glycine being electrically non-conductive.

The limited surgical access encountered during intracavitary endoscopic procedures makes the removal of tissue pieces derived from a typical electrosurgical loop cutting electrode both difficult and time consuming. Vaporisation of tissue whereby the tissue is reduced to smoke and water vapour is a preferable technique in these situations, rather than the piecemeal removal of tissue. The products of vaporisation may be removed following dissolution within a liquid irrigating medium.

With regard to underwater endoscopic electrosurgery, the applicants have found that it is possible to use a conductive liquid medium such as normal saline in place of glycine. Normal saline is the preferred distension medium in underwater endoscopic surgery when electrosurgery is not contemplated or a non-electrical tissue effect such as laser treatment is being used. Although normal saline (0.9%w/v; 150 mmol/l) has an electrical conductivity somewhat greater than that of most body tissue, it has the advantage that displacement by absorption or extravasation from the operative site produces little physiologicai effect and the so-called water intoxication effects of glycine are avoided.

Effective electrosurgical treatment of tissue which is totally immersed in liquid at the application site is difficult to achieve because the heat generated by the flow of electrical currents in both the tissue being treated and surrounding conductive liquid tends to cause boiling of the liquid. The operating electrode is intermittently surrounded by water vapour rather than liquid, with consequent large variations in the electrical impedance of the load presented to the generator supplying the electrosurgical power to the electrode. Whilst this variation is mitigated by use of a non-conductive liquid, it cannot be eliminated entirely due to the release of body fluids at the operative site which elevates the electrical conductance of the liquid. Changes in tissue type also alter the load impedance. These effects result in difficulty in controlling the electrosurgical output to produce consistent effects on the tissue being treated. As a result, high powers are commonly employed to overcome this performance variation.

SUMMARY OF THE INVENTION

According to a first aspect of this invention, an electrosurgical generator for supplying radio frequency power to an electrical instrument, comprises a radio frequency output stage having at least a pair of electrosurgical output connections for the delivery of radio frequency power to the instrument, a power supply coupled to the output stage for supplying power to the output stage, and control circuitry including sensing means for deriving a sensing signal representative of the radio frequency peak output voltage developed across the output connections, wherein the output stage comprises a resonant output circuit coupled to the output connections and a switching device coupled to the resonant output circuit, and wherein the control circuitry is operable to actuate the switching device to reduce the delivered radio frequency power. The switching device is preferably connected between the resonant output circuit and one of a pair of supply rails of the power supply means, and connected so as to switch current repeatedly through the resonant output circuit at its resonant frequency. In order to cause a control overshoot, in terms of the degree to which the delivered power is reduced when the output voltage reaches the predetermined threshold. The control circuitry is so arranged and coupled to the switching device that it is capable of reducing the "on" time of the switching device during individual radio frequency switching cycles sufficiently rapidly to cause a 50% reduction in delivered output power within 100 $\mu$s of the predetermined threshold having been reached. This allows surgery to be performed in a conductive fluid field, in particular in a saline solution. Large and rapid changes in load impedance can occur substantially without causing unwanted electrosursical effects. For example, when it is desired to produce electrosurgical desiccation, any increase in impedance due to vaporisation of surrounding saline in the region of an electrode of the instrument which might otherwise lead to unwanted arcing at the required power level for effective desiccation can be largely prevented. When electrosurgical tissue cutting or tissue vaporisation is required, output voltage limitation can be used to prevent electrode burning and/or excessive tissue vaporisation.

The control circuitry may include a control line feeding a first power reduction control signal to the radio frequency output stage. The output stage, which may be a radio frequency power oscillator, typically has as the oscillating element a radio frequency power device, and in the preferred embodiment, the control circuitry is arranged such that at least a 50% reduction in output power is brought about in a period of less than 20 $\mu$s after the output voltage reaches the predetermined threshold by reducing the period of conduction of the device during individual cycles of the radio frequency output signal. Such alteration in the period of conduction is advantageously achieved independently of any variation in supply voltage to the radio frequency power device. In practice, the reduction in output power is brought about using a single control variable, i.e. the peak output voltage or peak-to-peak output voltage, independently of supply voltage and independently of the delivered output power which varies according to the load impedance and the supply voltage. Thus, triggering of a power reduction occurs at the same preset output voltage threshold but at different output power and load impedance values, according to circumstances.

As an adjunct to direct control of the radio frequency output stage, the means for causing a reduction in output power may include a further control line which is coupled to the power supply means, the control circuitry being arranged such that a second power reduction signal is fed to the power supply means to effect a reduction in the average power supply voltage supplied to the output stage. Typically, the rate of reduction of power due to lowering of the power supply voltage is comparatively slow, but the combination of two means of control can produce a larger range of available output power levels.

Thus, according to a second aspect of the invention, there is provided an electrosurgical generator for supplying power to an electrosurgical instrument, the generator comprising a radio frequency output stage including a radio frequency power device and having at least a pair of electrosurgical output connections for delivery of radio frequency power to the instrument, a power supply coupled to the output stage, and control circuitry including sensing means for deriving a sensing signal representative of the load impedance across the output connections, the control circuitry having a first output coupled to the power device to reduce the radio frequency duty cycle thereof and a second output coupled to the power supply to effect a reduction in the average power supply voltage supplied to the output stage, the said reductions occurring in response to the sensing signal reaching a predetermined threshold value.

In the case of the power supply means being a switched mode power supply having output smoothing components, the supply circuit may be arranged such that the second power reduction control signal has the effect of disabling the supply circuit, e.g. by gating the pulsed output. Accordingly, a high-speed control response is obtained with the supply voltage falling relatively slowly after the initial step power reduction to enable the radio frequency duty cycle of the power device to be increased again, thereby allowing further high-speed power reductions if necessary.

The technique of directly controlling the radio frequency output stage can be performed by repeatedly producing, firstly, a rapid reduction in the cycle-by-cycle conduction period of the power device from a peak level to a trough level when the output threshold is reached, followed by, secondly, a progressive increase in the conduction period until the conduction period again reaches its peak level, the radio frequency output voltage being monitored during the progressive increase. This rapid reduction and progressive increase sequence may be repeated until the peak conduction period level can be reached without the output voltage exceeding the output threshold due to the supply voltage from the switched mode power supply having fallen sufficiently since it was disabled. Re-enabling of the supply circuit typically occurs after a delay, and conveniently at the end of the first switched mode switching cycle in which the output voltage has not reached the threshold for the whole of the switching cycle.

The output stage preferably includes an output resonant circuit having a Q which is sufficiently high to remove switching noise from the switching device or devices of the stage without unduly slowing the response to the output voltage reaching the predetermined threshold. Typically, the Q is sufficient to achieve a crest factor below 1.5, the crest factor being the ratio of the peak and r.m.s. values of the output voltage waveform.

Other aspects of the invention include a generator for underwater electrosurgery having an output impedance in the range of from 100 ohms to 250 ohms, and preferably between 130 and 190 ohms. Such a generator has its radio frequency output stage operable to produce a CW (continuous wave) output, i.e. with a 100% duty cycle or without on/off pulse width modulation at a frequency lower than the r.f oscillation frequency. In effect, the output stage may operate as an open loop stage with a power/load impedance characteristic having a peak (preferably a single peak) at about 150 to 160 ohms and with the curve decreasing continuously with decreasing impedance below the peak and increasing impedance above the peak.

The invention may also include an electrosurgical generator for supplying radio frequency power to an electrosurgical instrument for operation in an electrically conductive fluid medium, the generator comprising a radio frequency output stage having a radio frequency power device and at least a pair of electrosurgical output connections for the delivery of radio frequency power to electrodes, power supply means coupled to the output stage, and control circuitry including sensing means for deriving a sensing signal representative of the radio frequency output voltage developed across the output connections, and means responsive to the sensing signal for causing a reduction in delivered output power when the sensing signal is indicative of a predetermined output voltage threshold having been reached, wherein the control circuitry is arranged such that the reduction in output power is effected by reducing the period of conduction of the device during individual cycles of radio frequency oscillation, preferably independently of the supply voltage to the device.

According to another aspect to the invention, an electrosurgical generator for supplying electrosurgical power to an electrosurgical instrument comprises a radio frequency output stage having at least a pair of electrosurgical output connections for the delivery of radio frequency power to the instrument means coupled to the output stage for supplying power to the output stage, and control circuitry including sensing means for deriving a sensing signal representative of the radio frequency output voltage developed across the output connections and means responsive to the sensing signal for causing at least a 50% reduction in delivered output power when the sensing signal is indicative of a predetermined output voltage threshold having been reached, the said reduction being effected within a period of 20 $\mu$s or less.

The invention also includes an electrosurgical system including a generator for generating radio frequency power and an electrosurgical instrument having at least one electrode for use immersed in a conductive liquid, wherein the generator comprises an output stage including a radio frequency power device and at least a pair of output connections arranged to receive radio frequency power from the power device, one of the pair of connections being connected to the said electrode, and wherein the generator further comprises a control stage operable to reduce the conduction time of the power device during individual radio frequency cycles in response to a sensing signal (preferably the peak output voltage) representative of the load impedance presented to the generator across the output connections exceeding a predetermined sensing signal threshold value, whereby the radio frequency power delivered to the electrode structure is rapidly reduced when the conductive liquid is vaporised, The electrode structure may include a distal treatment electrode and a liquid contact electrode spaced proximally from the distal electrode, both electrodes being for use surrounded by the conductive liquid and each being connected to a respective one of the pair of output connections the control stage being operable to reduce the reduction time of the power device when the conductive liquid at the distal electrode is vaporised. The electrosurgical instrument may provide an electrode structure having juxtaposed first and second electrodes for immersion in the conductive liquid, the first and second electrodes respectively forming a tissue contact electrode at an extreme distal end of the instrument and a return electrode proximally spaced from the tissue contact electrode.

According to yet another aspect of the invention, there is provided an electrosurgical system operable in at least a tissue desiccation mode and a tissue cutting or vaporisation mode comprising a generator for generating radio frequency power and an electrosurgical instrument coupled to the generator, the instrument having an electrode structure for operation immersed in a conductive liquid, wherein the generator includes a mode selection control and has power control circuitry for automatically adjusting the radio frequency power suppled to the electrode structure to limit the peak generator output voltage to a first value when the desiccation mode is selected and to at least one second value when the cutting or vaporisation mode is selected, the second value or values being higher than the first value. The first and second values are advantageouslv in the ranges of from 150V to 200V, and from 250V to 600V respectively, these voltages being peak voltages.

From a method aspect, the invention provides a method of operating an electrosurgical system having at least a tissue desiccation mode and a tissue cutting or vaporisation mode, the system having a radio frequency power generator coupled to an electrode assembly having an electrode for operation in a conductive liquid, wherein the method comprises: selecting one of the said modes; when the desiccation mode is selected, automatically adjusting the radio frequency power supplied to the electrode assembly to maintain the conductive liquid adjacent the electrode at its boiling point for tissue desiccation without creating a vapour pocket surrounding the electrode; and when the cutting or vaporisation mode is selected, automatically adjusting the radio frequency power supplied to the electrode to maintain a vapour pocket surrounding the electrode. In the cutting or vaporisation mode the radio frequency power supply to the electrode may be automatically limited to prevent electrode overheating or erosion. The radio frequency power supply to the electrode may be automatically adjusted by limiting the output voltage to predetermined first and second voltage values, the first voltage value being used in the desiccation mode and the second voltage value, which is higher than the first voltage value, being used in the cutting or vaporisation mode.

The invention also provides a method of operating an electrosurgical system which has a generator coupled to an electrode assembly having an electrode for operation in a conductive liquid, wherein the method comprises applying radio frequency power to the electrode, monitoring an electrical signal related to the load impedance presented to the generator, and reducing the applied power when the said signal reaches a predetermined threshold value associated with an increased load impedance, whereby only sufficient radio frequency power is applied to the electrode to maintain the liquid adjacent the electrode at its boiling point for tissue desiccation without creating a vapour pocket surrounding the electrode.

According to a further aspect or the invention, an electrosurgical tissue desiccation method comprises: providing an electrosurgical system comprising an electrosurgical radio frequency generator coupled to an electrode assembly having a treatment electrode; introducing the electrode assembly into a selected operation site with the electrode contacting the tissue to be treated and with the tissue and the electrode immersed in a conductive liquid; actuating the generator; and controlling the radio frequency power applied to the electrode by the generator to maintain the conductive liquid adjacent the electrode at its boiling point without creating a vapour pocket surrounding the electrode.

According to yet a further aspect of the invention, there is provided an electrosurgical method comprising: providing an electrosurgical system comprising an electrosurgical radio frequency generator coupled to an electrode assembly having a treatment electrode; introducing the electrode assembly into a selected operation site with the electrode adjacent the tissue to be treated and with the tissue and the electrode immersed in a conductive liquid; actuating the generator and applying sufficient radio frequency power to the electrode to vaporise the conductive liquid surrounding the electrode; and controlling the radio frequency power applied to the electrode to maintain a layer of vapour around the electrode and to prevent electrode overheating.

BRIEF DESCRIPTION OF THE DRAWINGS

The invention is illustrated by way of example in the drawings in which:

FIG. 1 is a diagram showing an electrosurgical system in accordance with the invention;

FIG. 2 is a fragmentary view of a first electrode assembly for tissue desiccation, shown in use and immersed in a conductive liquid;

DETAILED DESCRIPTION OF THE PREFERRED EMBODIMENT

Figure 3:
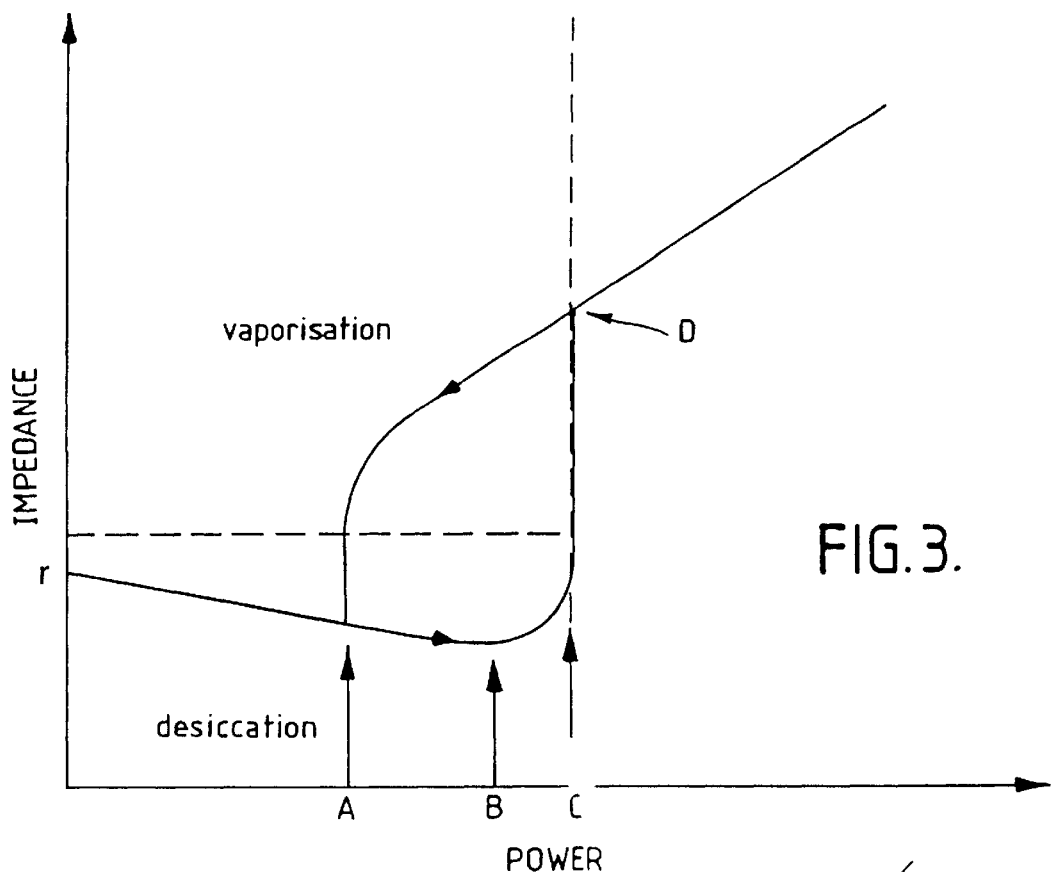
FIG. 3 is a load characteristic graph illustrating the variation in load impedance produced by an electrode assembly such as that shown in FIG. 2 When used in a conductive liquid, according to the delivered output power.

Historically, underwater electrosurgery has been the most demanding electrosurgical application in terms of instrument engineering. The reason for this is that the electrosurgical power requirement is very high, specifically because it is necessary to create arcs for cutting and tissue disruption in circumstances in which power is dissipated quickly by the surrounding liquid. Consequently, high currents are used to ensure vaporisation of liquid surrounding the electrode. Power levels up to 300 watts are commonly used. Conventionally, underwater electrosurgery is performed using a non-conductive fluid or irrigant to eliminate electrical conduction losses. Glycine, which is commonly used, has the disadvantage that in the course of an operation, veins may become severed and irrigant may be infused into the circulation. This absorption causes among other things a dilution of serum sodium which can lead to a condition known as water intoxication.

Accordingly, the applicants propose use of a conductive liquid medium such as normal saline, electrosurgery being performed with using a system comprising a generator and an instrument, the instrument having a dual-electrode structure with the saline acting as a conductor between the tissue being treated and one of the electrodes, hereinafter called the "return electrode". The other electrode is applied directly to the tissue. This other electrode is hereinafter called the "active electrode".

Such a system is shown in FIG. 1. The generator 10 has an output socket 10S providing a radio frequency (RF) output for an instrument in the form of a hand piece 12 via a connection cord 14. Activation of the generator may be performed from the hand-piece 12 via a control connection in cord 14 or by means of a footswitch unit 16, as shown, connected separately to the rear of the generator 10 by a footswitch connection cord 18. In the illustrated embodiment, footswitch unit 16 has two footswitches 16A and 16B for selecting a desiccation mode and a vaporisation mode of the generator respectively. The generator front panel has push buttons 20 and 22 for respectively setting desiccation and vaporisation power levels, which are indicated in a display 24. Push buttons 26 are provided as an alternative means for selection between desiccation and vaporisation modes.

Handpiece 12 mounts a detachable electrode assembly 28 having a dual electrode structure, as shown in the fragmentary view of FIG. 2.

FIG. 2 is an enlarged view of the distal end of electrode assembly 28. At its extreme distal end the assembly has an active electrode 30 which, in this embodiment, is formed as a series of metal filaments connected to a central conductor 32. The filaments may be made of stainless steel. Proximally of the active electrode 30 and spaced from the latter by a longitudinally and radially extending insulator 34 is a return electrode 36. The return electrode 36 is arranged coaxially around the inner conductor 32 as a sleeve which extends as a tubular shaft 40 to the proximal end of the assembly 28 where it is connected in the hand-piece 12 to conductors in the connection cord 14. Similarly, the inner conductor 32 extends to the handpiece and is connected to a conductor in cord 14. The electrode assembly 28 has an insulating sheath 42 which covers shaft 40 and terminates proximally of the insulator 34 to leave the distal end of shaft 40 exposed as the return electrode 36.

In operation as a desiccation instrument, the electrode assembly 28 is applied as shown in FIG. 2 to the tissue 44 to be treated, the operation site being immersed in a normal saline (0.9%w/v) solution, here shown as a drop 46 of liquid surrounding the distal end portion of the electrode assembly 28. The liquid immerses both the active electrode 30 and the return electrode 36.

Still referring again to FIG. 2, the metallic filaments forming the active electrode 30 are all electrically connected together and to the inner conductor 32 of the electrode assembly to form a unitary active electrode. Insulator 34 is an insulating sleeve, the distal end portion of which is exposed proximally of the exposed part of the active electrode 30. Typically, this sleeve is made of a ceramic material to resist damage from arcing. The return electrode terminates at a point short of the end of the insulator 36 so that it is both radially and axially spaced from the active, or tissue contact, electrode 30. The surface area of the return electrode is considerably greater than that of the active electrode 30. At the distal end of the electrode assembly, the diameter of the return electrode is typically in the region of from 1 mm to 3 mm, with the longitudinal extent of the exposed part of the return electrode being typically between 1 mm and 5 mm with the longitudinal spacing from the active electrode being between 1 mm and 5 mm.

In effect, the electrode assembly is bipolar, with only one of the electrodes (30) actually extending to the distal end of the unit. This means that the return electrode, in normal circumstances, remains spaced from the tissue being treated and a current path exists between the two electrodes via the tissue and the conductive liquid which is in contact with the return electrode 36.

The conductive liquid 46 may be regarded, as far as the delivery of bipolar electrosurgical energy is concerned, as a low impedance extension of the tissue. Radio frequency currents produced by the generator 10 flow between the active electrode 30 and the return electrode 36 via the tissue 44 and the immersing conductive liquid 46. The particular electrode arrangement shown in FIG. 2 is most suitable for tissue desiccation.

The axial as well as radial separation between the electrodes avoids the small spacing of the conventional bipolar arrangement in which both electrodes are tissue-contacting. As a result, there is less danger of unwanted arcing across the insulation surface, which allows comparatively high power dissipation for desiccation treatment, and, in the case of tissue cutting or vaporisation, prevents excessive arcing which can lead to inter-electrode insulation damage.

The immersing saline solution may be provided from a conduit (not shown) forming part of the instrument 12. Thus, the invention may take the form of an electrosurgical system for the treatment of tissue immersed in a conductive fluid medium, comprising an electrosurgical instrument having a handpiece and an instrument shaft, and, on the end of the shaft, an electrode assembly the assembly comprising a tissue contact electrode which is exposed at the extreme distal end of the instrument, and a return electrode which is electrically insulated from the tissue contact electrode and has a fluid contact surface spaced proximally from the exposed part of the tissue contact electrode, the system further comprising a radio frequency generator coupled to the electrode assembly of the instrument, a reservoir of electrically conductive fluid, such as the normal saline solution, and a conduit, typically and integral part of an endoscope, for delivering the liquid from the reservoir to the region of the electrode assembly. Pressure for delivering the liquid may be provided by a pump forming part of the apparatus.

Since in this embodiment of electrode assembly 28, the active electrode 30 is made of stainless steel filaments in the form of a brush, the electrode is flexible, providing a reproducible tissue effect which is comparatively independent of the application angle of the electrode to the tissue surface. The flexibility of the electrode 30 also results in a differential contact area of the active electrode dependent on the applied pressure, following variations in the breadth of desiccation over the surface of the tissue, reducing procedure time.

Desiccation occurs by virtue of radio frequency currents passing between the active electrode 30 and the conductive liquid 46 via the outer layer of the tissue 44 immediately beneath and in an area surrounding the active electrode 30. The output impedance of the generator is set at a level commensurate with the load impedance of the electrode assembly when used as shown in FIG. 2 with both electrodes in contact with the conductive liquid 46. In order to sustain this matched state for tissue desiccation, the output power of the generator is automatically controlled in a manner which will be described below so that vapour bubbles of significant size are substantially prevented from appearing at the active electrode 30, thereby avoiding a consequent increase in load impedance. In this way, the active electrode can be continually wetted by the conductive liquid so that, whilst the tissue water is removed by thermal desiccation, the impedance reaches an upper limit corresponding to the point at which the conductive liquid starts to boil. As a result, the system is able to deliver high power levels for desiccation without unwanted conductive liquid vaponrsation leading to unwanted tissue effects.

The electrical behaviour of the electrode assembly when the electrodes 30 and 36 are immersed in the conductive liquid 46 is now considered with reference to the graph of FIG. 3.

When power is first applied, there is presented to the generator an initial load impedance r which is governed by the geometry of the electrode and the electrical conductivity of the conductive liquid. The value of r changes when the active electrode touches the tissue. The higher the value of r, the greater is the propensity of the conductive liquid to vaporise. As power is dissipated in the tissue and the conductive liquid, the conductive liquid increases in temperature. In the case of normal saline, the temperature coefficient of conductivity is positive and the corresponding impedance coefficient is therefore negative so that the impedance initially falls. Thus, the curve in FIG. 3 indicates a fall in load impedance as the delivered power is increased, the impedance falling through point A to a minimum at point B, at which point saline in immediate contact with the electrode reaches boiling point. Small vapour bubbles now form on the surface of the active electrode and the impedance starts to rise as shown by the curve rising from point B to point C. Thus, once the boiling point has been reached, the arrangement displays a dominant positive power coefficient of impedance.

As the vapour bubbles form, there is an increase in the power density at the remaining active electrode to saline interface (the exposed area of the active electrode not covered by vapour bubbles) which further stresses the interface, producing more vapour bubbles and thus even higher power density. This is a runaway condition, with an equilibrium point only occurring once the electrode is completely enveloped in vapour. Thus, for a given set of variables, there is a power threshold corresponding to point C at which this new equilibrium is reached.

In the light of the foregoing, it will be appreciated that the region between points B and C in FIG. 3 represents the upper limit of desiccation power which can be achieved.

Upon formation of an electrode-enveloping vapour pocket, the impedance elevates to about 1 kΩ, as shown by point D in FIG. 3, the actual impedance value depending on a number of system variables. The vapour is then sustained by discharges across the pocket between the active electrode and the vapour/saline interface.

Figure 4:
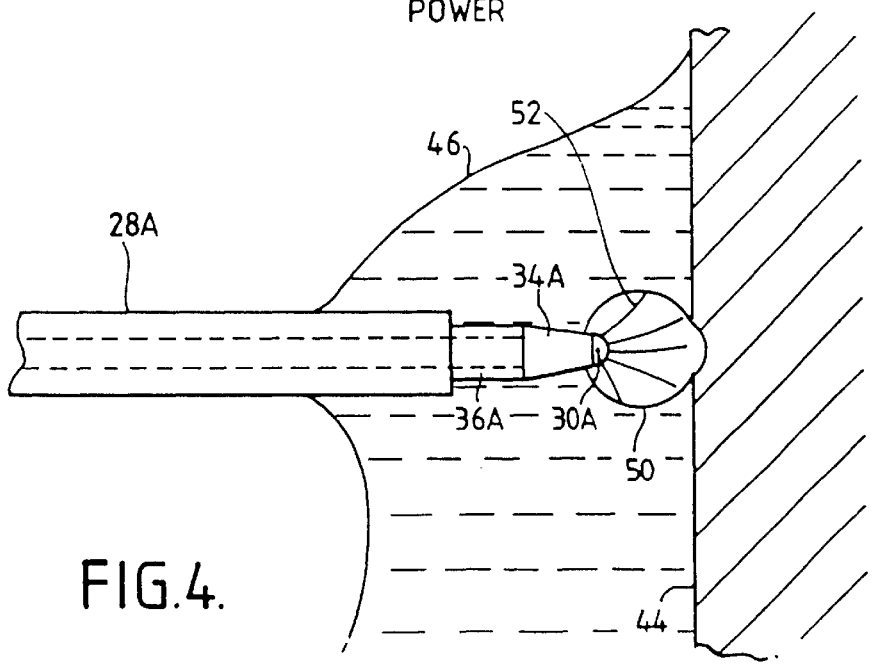
FIG. 4 is a fragmentary view of a second electrode assembly for tissue vaporisation, shown in use immersed in a liquid.

This state of affairs is illustrated by the diagram of FIG. 4 which shows an alternative electrode assembly 28A having a hemispherical or ball electrode 30A in place of the brush electrode 30 of the embodiment of FIG. 2. As before, the return electrode 36A is proximally spaced from the active electrode 30A by an intervening insulator 34A. The ball electrode is preferred for tissue vaporisation.

Once in the vaporisation equilibrium state, the vapour pocket, shown by the reference 50 in FIG. 4, is sustained by discharges 52 across the vapour pocket between the active electrode 30A and the vapour to saline interface. The majority of power dissipation occurs within this pocket with consequent heating of the active electrode. The amount of energy dissipation in this conduction is a function of the delivered power. It will be noted from FIG. 3 that the vaporisation mode, indicated by the dotted boundary lines, can be sustained at much lower power levels than are required to bring about formation of the vapour pocket. The impedance power characteristic consequently displays hysteresis. Once the vaporisation mode has been established, it can be maintained over a comparatively wide range or power levels, as shown by the inclined part of the characteristic extending on both sides of point D. However, increasing the delivered output power beyond that represented by point D causes a rapid rise in electrode temperature, potentially damaging the electrode. To collapse the vapour pocket and to return to desiccation mode requires a significant power reduction back to point A, direct contact between the active electrode and the saline being reestablished and the impedance falling dramatically. The power density at the active electrode also falls so that the temperature of the saline now falls below boiling point and the electrode is then once again in a stable desiccation equilibrium.

The generator to be described hereinafter has the ability to sustain both the desiccation mode and the vaporisation mode. Whilst in general the electrode assemblies illustrated in FIGS. 2 and 4 can be used in either mode, the brush electrode of FIG. 2 is preferred for desiccation due to its wide potential area of coverage, and the ball electrode of FIG. 4 is preferred for vaporisation due to its small active electrode/return electrode surface area ratio. As can be seen from FIG. 4, tissue vaporisation occurs when the vapour pocket 50 intersects the tissue surface, with the electrode assembly preferably being held spaced above the tissue surface by a small distance (typically 1 mm to 5 mm).

The runaway condition which occurs when the delivered power reaches the level shown by point C in FIG. 3 is exacerbated if the generator has a significant output impedance, because the output voltage can then suddenly rise. With increased power dissipation and without the presence of the cooling liquid around the active electrode 30, the electrode temperature rises rapidly with consequent damage to the electrode. This also produces uncontrollable tissue disruption in place of the required desiccation. For this reason, the preferred generator has an output source impedance which, approximately at least matches the load impedance of the electrode structure when wetted.

The preferred generator now to be described allows both desiccation electrosurgery substantially without unwanted cell disruption, and electrosurgical cutting or vaporisation substantially without electrode burning. Although intended primarily for operation in a conductive liquid distension medium, it has application in other electrosurgical procedures, e.g. in the presence or a gaseous distension medium, or wherever rapid load impedance chances can occur.

Figure 5:
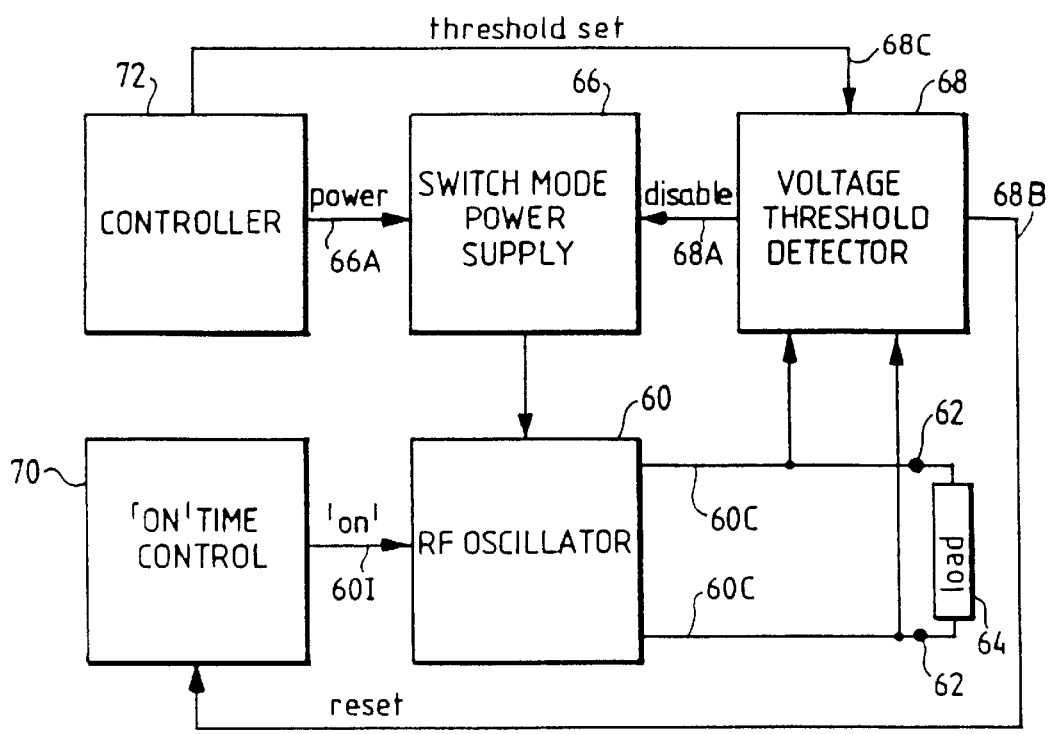
FIG. 5 is a block diagram of a generator in accordance with the invention.

Referring to FIG. 5, the generator comprises a radio frequency (RF) power oscillator 60 having a pair of output connections 60C for coupling via output terminals 62 to the load impedance 64 represented by the electrode assembly when in use. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output connections 60C is a voltage threshold detector 68 having a first output 68A coupled to the switched mode power supply 16 and a second output 68B coupled to an "on" time control circuit 70. A microprocessor controller 72 coupled to the operator controls and display (shown in FIG. 1), is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a handpiece or footswitch (see FIG. 1). A constant output voltage threshold is set via input 68C according to control settings on the front panel of the generator (see FIG. 1). Typically, for desiccation or coagulation the threshold is set at a desiccation threshold value between 150 volts and 200 volts. When a cutting or vaporisation output is required, the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. If the supply voltage is sufficiently high, the temperature of the liquid medium surrounding the electrodes of the electrosurgical instrument (or within a gaseous medium, the temperature of liquids contained within the tissue) may rise to such an extent that the liquid medium vaporises, leading to a rapid increase in load impedance and a consequent rapid increase in the applied output voltage across terminals 12. This is an undesirable state of affairs if a desiccation output is required. For this reason, the voltage threshold for a desiccation output is set to cause trigger signals to be sent to the "on" time control circuit 70 and to the switched mode power supply 66 when the threshold is reached. The "on" time control circuit 20 has the effect of virtally instantaneously reducing the "on" time of the RF oscillator switching device. Simultaneously, the switched mode power supply is disabled so that the voltage supplied to oscillator 60 begins to fall.

Figure 6:
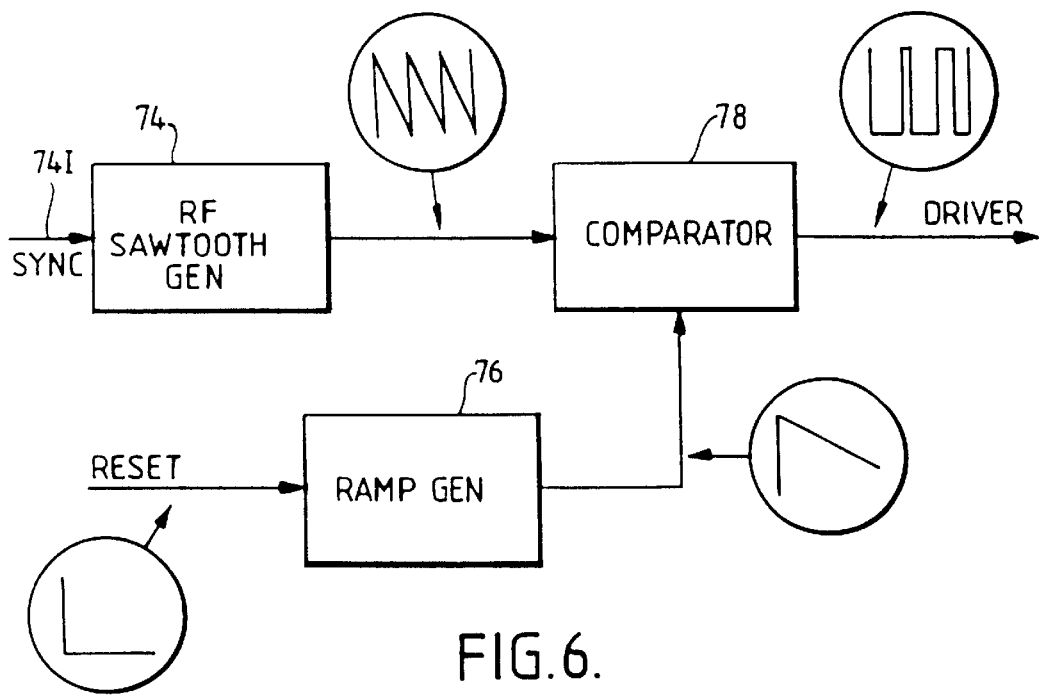
FIG. 6 is a block diagram of part of the control circuitry of the generator of FIG. 5.

Subsequent control of the "on" time of individual cycles of the oscillator 60 will be understood by considering the internal configuration of the "on" time control circuit 20 which is shown in FIG. 6. The circuit comprises an RF sawtooth generator 74 (synchronised at the RF oscillation frequency by a synchronisation signal derived from the oscillator and applied to a synchronisation input 74I), and a ramp generator 76 which is reset by a reset pulse from the output 68B of the voltage threshold detector 68 (see FIG. 5) produced when the set threshold voltage is reached. This reset pulse is the trigger signal referred to above. The "on" time control circuit 70 further comprises a comparator 78 for comparing the sawtooth and ramp voltages produced by the sawtooth and ramp generators 74 and 76 to yield a square wave control signal for application to the input 60I of the RF oscillator 60. As shown by the waveform diagrams in FIG. 6, the nature of the sawtooth and ramp waveforms is such that the mark-to-space ratio of the square wave signal applied to the oscillator 60 progressively increases after each reset pulse. As a result, after a virtually instantaneous reduction in "on" time on detection of the output voltage reaching the set voltage threshold, the "on" time of the RF oscillator is progressively increased back to the original maximum value. This cycle is repeated until the supply voltage for the oscillator from power supply 66 (FIG. 5) has reduced to a level at which the oscillator can operate with the maximum conduction period without the output voltage breaching the set voltage threshold as sensed by the detector 68.

The output voltage of the generator is important to the mode of operation. In fact, the output modes are defined purely by output voltage, specifically the peak output voltage. The absolute measure of output voltage is only necessary for multiple term control. However, a simple term control (i.e. using one control variable) can be used in this generator in order to confine the output voltage to predetermined limit voltages. Thus, the voltage threshold detector 68 shown in FIG. 5 compares the RF peak output voltage with a preset DC threshold level, and has a sufficiently fast response time to produce a reset pulse for the "on" time control circuit 70 within one RF half cycle.

Before considering the operation of the generator further, it is appropriate to refer back to the impedance/power characteristic of FIG. 3. It will be appreciated that the most critical control threshold is that applicable during desiccation, Since vapour bubbles forming at the active electrode are non-conducting, the saline remaining in contact with the electrode has a higher power density and consequently an even greater propensity to form vapour. This degree of instability brings about a transition to a vaporisation mode with the same power level due to the runaway increase in power density at the active electrode. As a result, the impedance local to the active electrode rises. Maximum absorbed power coincides with the electrode condition existing immediately before formation of vapour bubbles, since this coincides with maximum power distribution and the greatest wetted electrode area. It is therefore desirable that the electrode remains in its wetted state for the maximum desiccation power. Use of voltage limit detection brings about a power reduction which allows the vapour bubbles to collapse which in turn increases the ability or the active electrode to absorb power. For this reason, the generator described in this specification includes a control loop having a large overshoot, in that the feedback stimulus of the peak voltage reaching the predefined threshold causes a large instantaneous reduction in power. This control overshoot ensures a return to the required wetted state.

In the generator described above with reference to FIGS. 5 and 6, power reduction in response to voltage threshold detection takes place in two ways:

(a) an instantaneous reduction in RF energy supplied to the resonant output circuit of the oscillator, and (b) a shut down of DC power to the oscillator for one or more complete cycles of the switched mode power supply (i.e. typically for a minimum period of 20 to 40 $\mu$s).

In the preferred embodiment, the instantaneous power reduction is by at least three quarters of available power (or at least half voltage) from the DC power supply, but continuous voltage threshold feedback continually causes a reduction in delivered power from the DC power supply. Thus, a high speed response is obtained in the RF stage itself, with the DC supply voltage tracking the reduction to enable the RF stage to return to a full duty cycle or mark-to-space ratio, thereby enabling further rapid power reductions when the voltage threshold is again breached.

Figure 7:
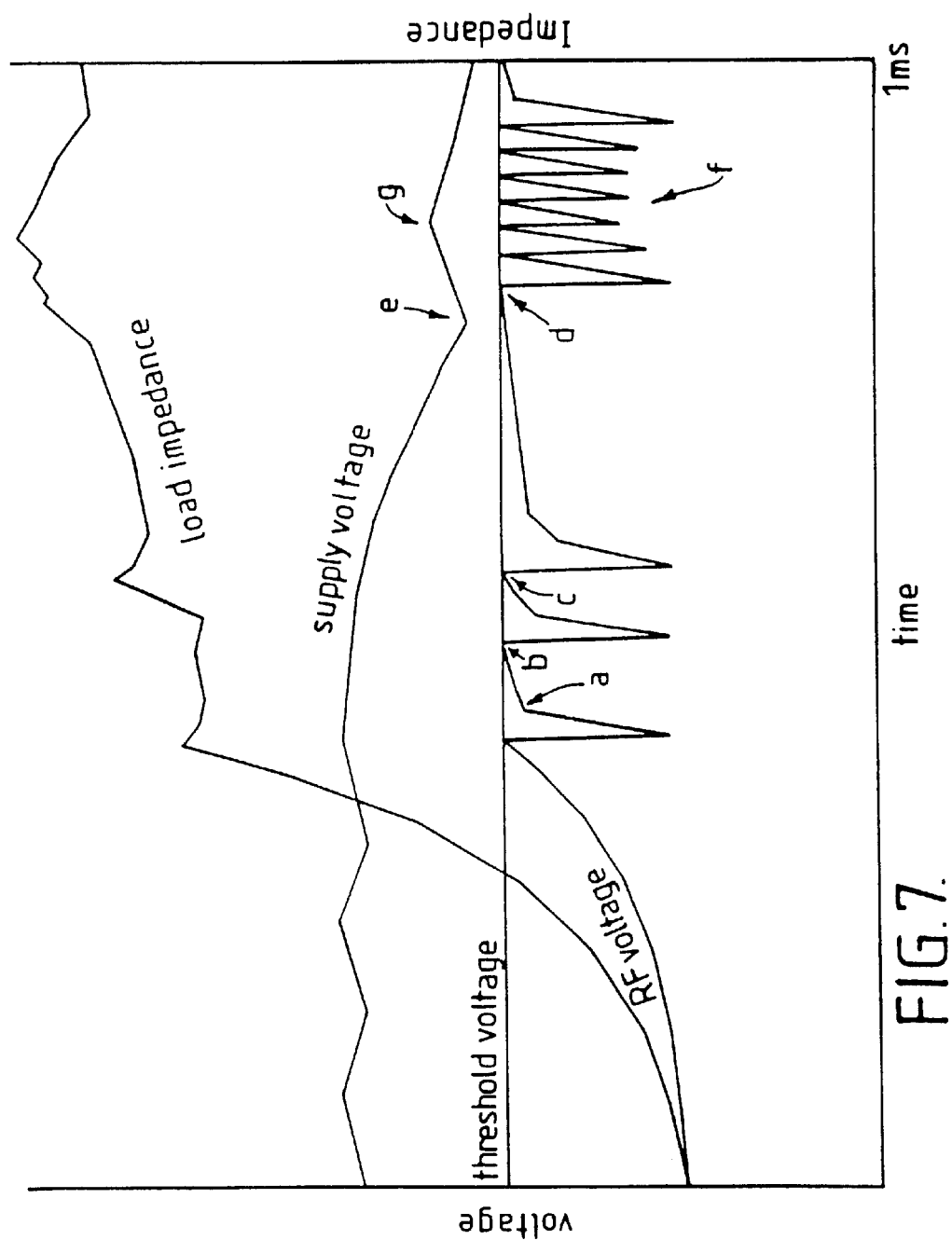
FIG. 7 is a waveform diagram showing a typical RF output voltage variation pattern obtained with the generator of FIGS. 5 to 7, the voltage being shown varying with time according to variations in load impedance and generator output stage supply voltage.

The effect of this process on the RF output voltage is shown in the waveform diagram of FIG. 7, containing traces representative of the output voltage, the oscillator supply voltage, and the load impedance during a typical desiccation episode over a 1 ms period.

Starting on the lefthand side of the diagram with the supply voltage approximately constant, the output voltage increases with increasing load impedance to a point at which the output voltage threshold is reached, whereupon the above-described instantaneous reduction in oscillator "on" time occurs. This produces a rapid decrease in the RF output voltage, as shown, followed by a progressive increase, again as described above. When the output voltage reaches the threshold voltage, the voltage threshold detector 68 (shown in FIG. 5) also disables the power supply, leading to a gradual decrease in the supply voltage. As a result, when the "on" time of the oscillator device has once again reached its maximum value, illustrated by point a in FIG. 7, the threshold voltage has not been reached. However, the load impedance begins rising again, causing a further, albeit slower, increase in the output voltage until, once again, the threshold voltage is reached (point b). Once more, the "on" time of the oscillator is instantly reduced and then progressively increased, so that the output voltage waveform repeats its previous pattern. Yet again, the threshold voltage is reached, again the output voltage is instantly reduced (at point c), and again the "on" time is allowed to increase. On this occasion, however, due to the supply voltage having further reduced (the power supply still being disabled). the output voltage does not reach the threshold level (at point d) until a considerably longer time period has elapsed. Indeed, the length of the period is such that the output voltage has failed to reach the threshold voltage over a complete switching cycle of the power supply, so that it has in the meantime been enabled (at point e).

During this period the power supplied to the electrode has been sufficient to further increase the load impedance. The erratic impedance behaviour is typical of the commencement of vapour formation. Consequently, when the threshold voltage is next reached (at point e), several successive cycles of "on" time reduction and increase occurring one after the other are required (see f) combined with a further disabling (see g) of the power supply in order to maintain the voltage below the threshold.

It will be seen, then, that the control circuitry 70, 72 (FIG. 5) operates dynamically to control the output voltage both sufficiently rapidly and to a sufficient degree to maintain the voltage at a level consistent with, in this case, the level required for desiccation without tissue disruption due to arcing. The same technique can be used with a different threshold voltage to limit the output voltage to prevent electrode burning and/or excessive tissue vaporisation. In the latter case, the voltage limit may be set to a level between 250 volts (preferably 300 volts) and 600 volts.

Due to the high power density at the active electrode during the vaporisation mode, the great majority of delivered power is dissipated in the proximity of the electrode. In the vaporisation mode, it is desirable that a minimum of saline heating occurs, but that any tissue which encroaches the vapour boundary of the active electrode is vaporised. In the vaporisation mode, the vapour is sustained by arcs within the vapour pocket as described above with reference to FIG. 4, Increasing the output voltage during vaporisation results in increased volume of tissue removal due to the increased size of the vapour pocket. Collapse of the vapour pocket during tissue vaporisation has greater consequence, due to the increased necrosis as a result of the greater power dissipation in the surrounding saline. Vapour pocket collapse can be prevented by, firstly, arranging for the electrode impedance in vaporisation mode to be such that the instrument is in an unmatched condition as regards impedance, with result that the resonant output circuit Q is high and the output voltage does not change so rapidly as with lower load impedances and, secondly, the active electrode has a significant heat capacity that sustains the vapour pocket for a significant period.

An unwanted increased in the size of the vapour pocket can be prevented by limiting the peak output voltage during the vaporisation mode, which may be conveniently carried out by substituting a different threshold value for the voltage threshold detector 68 (see FIG. 5) when in the vaporisation mode.

Figure 8:
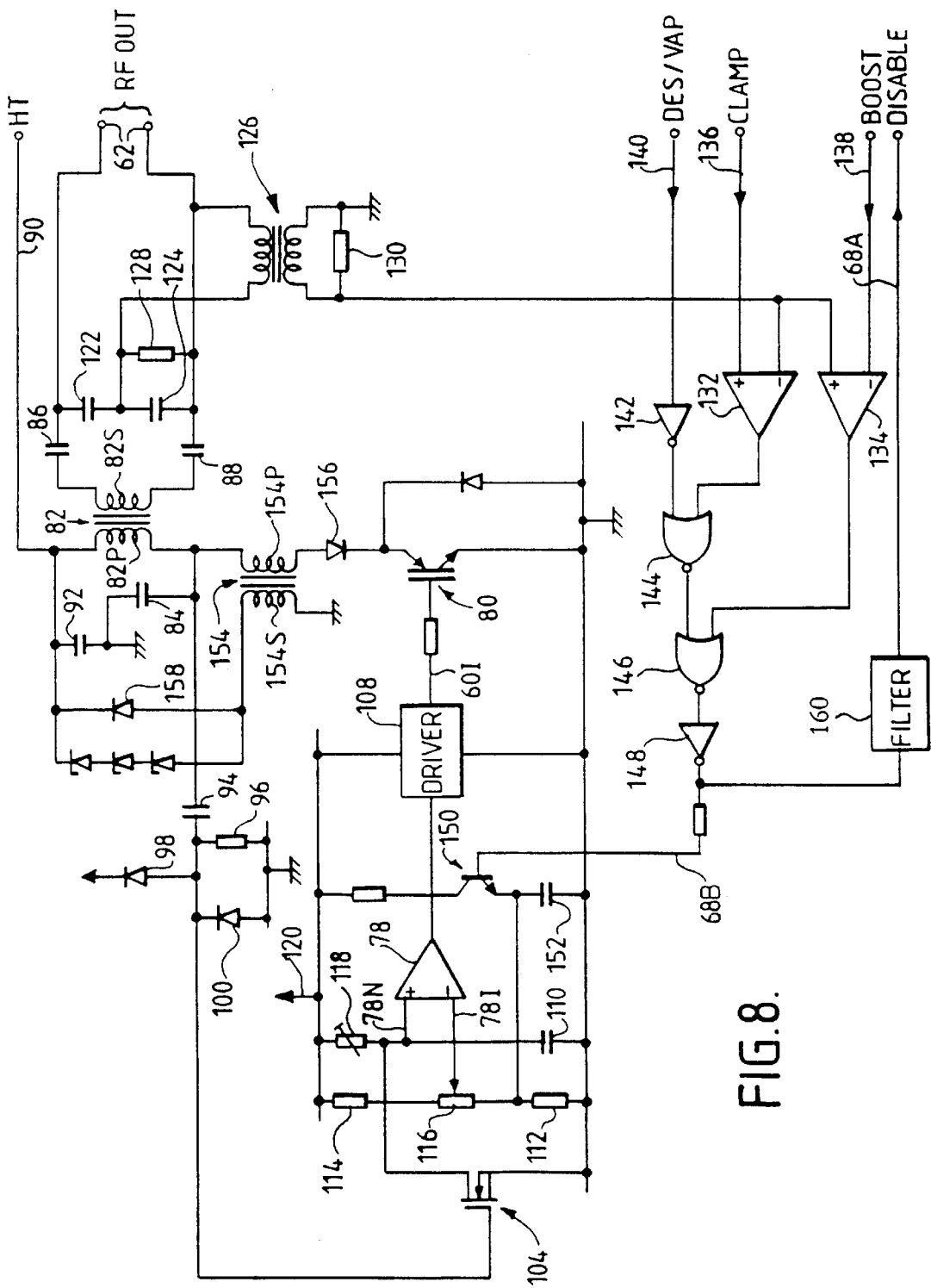
FIG. 8 is a circuit diagram of part of the generator of FIGS. 5 and 6.

The circuitry of the RF oscillator 60, voltage threshold detector 68, and "on" time control circuit 70 (shown in FIG. 5) in the preferred generator in accordance with the invention is shown in FIG. 8.

Referring now to FIG. 8, the RF oscillator comprises an IGBT (insulated gate bipolar transistor) 80 acting as an RF switching device which pumps energy into a parallel resonant circuit comprising the primary winding 82P of transformer 82 and a parallelconnected resonating capacitor 84. RF power is supplied from the transformer secondary winding 82S via isolating capacitors 86, 88 to RF output terminals 62. Power for the oscillator transistor 80 is supplied on a high voltage supply line 90 which is connected to the output of the switched mode power supply 66 (shown in FIG. 5). Supply line 90 is decoupled by capacitor 92

The oscillator feedback loop runs from the resonant primary winding 82P (on the opposite side of the winding from the supply line 90) via a phase shift network comprising capacitor 94, resistor 96, and clamping diodes 98, 100, and via a field effect transistor (FET) 104, the voltage controlled monostable represented by comparator 78 and associated components, and the driver 108, which is connected to the gate of transistor 80.

The voltage on that side of the primary winding 82P which is coupled to transistor 80 is substantially sinusoidal and alternates at a frequency defined by the parallel resonant combination of the winding inductance and capacitor 84. Typically the voltage swing is greater than twice the supply voltage on supply line 90, falling below ground voltage in negative half-cycles.

The phase-shift network 94, 96, 98, 100 provides a positive-going square wave which is 90° phase-advanced with respect to the primary voltage. Thus, FET 104 is turned on approximately when the voltage on primary winding 82P has just reached its minimum value, and off when it has just reached its maximum value. When FET 104 is turned on a timing capacitor is rapidly discharged and the output of comparator 78 is turned off. The driver 108 is non-inverting and consequently transistor 80 is also turned off at this point. It follows that the transistor "off" point is repeatable and has a constant phase relationship with respect to the primary voltage by virtue of the feedback path described above. The logic of the feedback path is also such that the feedback signal fed to the gate connection of transistor 80 has a logic level of "1" when the primary voltage is decreasing (and the potential difference across the primary winding 82P is increasing). The "off" point occurs substantially at a primary voltage peak, i.e. when the primary voltage is at its minimum value in the present case.

Unlike the "off" point, the "on" point of transistor 80 is variable as will now be described. The instant at which the logic level at the output of comparator 78 and on the base of device 80 changes to "1" depends on the reference voltage applied to the inverting input 78I of comparator 78. As a result, the delay between device 80 switching off and switching on is determined by this comparison of voltage applied to input 78I of comparator 78. In other words, an "on" signal to device 80 is delayed with respect to switching off by a period which is in accordance with the reference voltage on the inverting input, This reference voltage is dependent on the voltage appearing across resistor 112 which is part of a potential divider consisting also of resistor 114 and potentiometer 116. Potentiometer 116 sets the minimum switching on delay corresponding to the maximum duty cycle of transistor 80. The voltage appearing across resistor 112 is variable and represents the control range of "on" time adjustment between 25% of the maximum duty cycle and 100%. Timing capacitor 110 is charged by variable resistor 118 (preset for an appropriate time constant) from a low voltage supply line 120.

Comparing FIG. 8 with FIG. 6, it will be appreciated that the voltage on the non-inverting input 78N of comparator 78 has a sawtooth waveform as shown in FIG. 6, the waveform being produced by the repeated triggering of FET 104 and discharging of capacitor 110, each discharging being followed by charging of a capacitor through resistor 118.

The voltage across resistor 112 is normally at a minimum value, and is increased when the RF output voltage from the generator reaches a predetermined peak threshold value. The circuitry which brings about this effect will now be described.

Output voltage detection is provided by the capacitive divider chain 122, 124 connected across the RF output, the tap between the capacitors feeding the primary winding of an isolating transformer 126. Resistors 128 and 130 connected across the primary and secondary windings of transformer 126 respectively provide damping to avoid unwanted resonances and to filter high frequency components which may occur during arcing at the active electrode. The resulting sensing voltage appearing at the secondary winding of transformer 126 is then fed to two comparators 132 and 134. At this point, it should be appreciated that only the positive-going half cycles of the sense voltage are used for peak output voltage threshold detection.

Each comparator 132, 134 has two inputs, one connected to the transformer 126 to receive the sense voltage, and one connected to a respective reference voltage input 136, 138 (labelled CLAMP and BOOST in FIG. 8). Reference voltages applied to these inputs 136, 138 are computer generated set voltage thresholds for the desiccate and vaporisation modes respectively. Selection of the operating mode is brought about by a control signal (DES/VAP) applied to control input 140, and the logic chain comprising gates 142, 144, 146, and 148. Desiccation mode is set by logic level "1" at input 140. In vaporisation mode, logic level "0" on this input effectively disables the output of comparator 132 via NOR gate 144, the output threshold detection then being fed through NOR gate 146. It will therefore be appreciated that the CLAMP voltage applied to input 136 is the reference voltage setting the threshold value for the peak output voltage during desiccation, while the BOOST voltage applied to input 138 sets the threshold value of the peak output voltage in the vaporisation mode.

When the output voltage reaches the set threshold value (i.e. a "limit" voltage), transistor 150 is switched on. This transistor is capable of charging capacitor 152 from 1.5V to 4V in a period of 50 ns. The base charge of transistor 150 is sufficient to enlarge very narrow pulses from the voltage detection circuitry and therefore ensures that capacitor 152 attains maximum voltage for only marginly detected limit voltages at the RF output. The function of capacitor 152 is to provide progressively lower reference voltages for comparator 78 after a limit voltage detection. Thus, the voltage on the emitter of transistor 150 has a waveform as shown at the output of the ramp generator 76 in FIG. 6. In this way, the turn-on instant of device 80 is instantly retarded when the RF output voltage reaches the preset threshold value, and is subsequently progressively advanced as the voltage across resistor 112 slowly decreases. The discharge rate of capacitor 152 is determined by the parallel combination of resistor 112 in parallel with resistor 114 plus resistor 116.

Switching energy provided by transistor 80 is converted by a series inductor 154P into a current drive into the resonant primary winding 82P. The action of series inductor 154P smoothes energy injection into the resonant output circuit represented by winding 82P and capacitor 84 and prevents excessive initial current through transistor 80, and excessive swinging of the voltage input to winding 82P above the voltage on supply line 90.

Under full power conditions, the initial switch-on of transistor 80 occurs at an initial resonant voltage maximum across the resonant circuit. This creates a switch-on current zero as the inductor 154P is completely depleted of energy after each cycle. Current in this inductor rapidly builds up until a point is reached at which the voltage on winding 82P becomes negative. The inductor 154P then releases its energy into this reverse bias. The current zero at switch-off is then guaranteed by a blocking diode 156 which prevents the return of energy from the resonant circuit to the inductor 154P.

When the switch-on time of transistor 80 is reduced due to the output voltage reaching the predetermined set threshold, the primary voltage amplitude across winding 82P decreases to the extent that the primary peak amplitude is less than the supply voltage. In particular, the voltage minimum at the end of primary winding 82P coupled to transistor 80 no longer swings beyond the ground voltage. Energy can now no longer be released from inductor 154P back into the resonant circuit. A secondary path for stored energy in inductor 154P is provided by the fact that this inductor is the primary winding of a transformer 154 which has a second winding 154S coupled via a diode 158 to the supply line 90. Residual energy stored in inductor 154P at switch-off causes forward biasing of diode 158 through which the energy is recovered back into the supply. This recovers mechanism permits partial resonant primary amplitude levels without damaging switching transistor 80 by uncoupled energy creating excessive voltage.

The relationship between "on" time of transistor 80 and switching energy depends on a number of variables such as the initial energy storage of the resonant circuit 82P, 84, the loading on the output terminals 62 (which affects the Q of the resonant circuit), and the loading as it affects oscillation frequency, which all affect the non-linear energy storing rate of inductor 154P.

As has been described above, detection of the output voltage reaching a predetermined threshold value not only causes the duty cycle of the switching transistor 80 to be instantly reduced, but it also disables the switched mode power supply 66 (shown in FIG. 5). This disabling effect is produced by feeding a signal from the output of the logic chain 142 to 148 via a filter 160 to remove RF transients to a DISABLE output 68A, which is connected to the switched mode power supply 66.

The generator output impedance is set to about 160 ohms. The effect of this choice will be evident from the following description with reference to FIGS. 9 and 10 which are graphs showing the variation of output power which can be produced by the generator into different load impedances.

Figure 9:
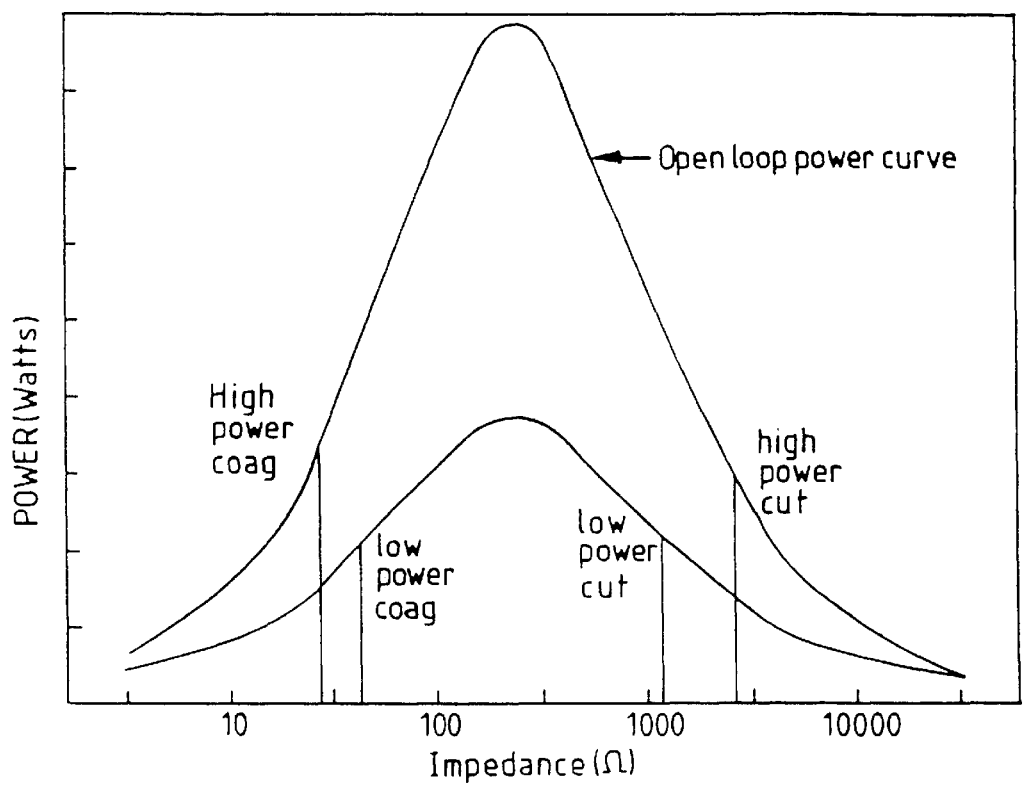
FIG. 9 is a graph showing the variation of output power produced by the generator as a function of the load impedance presented to it by the electrode assembly, the output power variation being shown in two operation modes of the generator.

Referring to FIG. 9, the power delivered to the load is here shown as a function of load impedance for two different oscillator supply voltage settings. In both cases, it will be seen that, to the left of the power/impedance peak, an increase in load impedance leads to an increase in output power and, hence, an increase in output voltage. At higher impedances, to the right of the peaks the voltage continues to increase, albeit less aggressively, as impedance increases.

One of the features of the preferred generator in accordance with the invention is that the output stage operates as an open loop oscillator with an output impedance (corresponding to the peaks in FIG. 9) of about 160 ohms. This is considerably lower than the output impedance of conventional generators used for underwater electrosurgery, and contributes to the ability to prevent runaway arcing behaviour and consequent excessive tissue damage and electrode burn-out.

It should be understood that for desiccation, steam envelope generation at the electrode and arcing should be prevented. Conversely, for cutting or vaporisation, steam envelope veneration and arcing are required, but to a level consistent with achieving the required tissue effect and the avoidance of electrode burn-out. Operating points for low and high power desiccation and cutting or vaporisation are shown in FIG. 9.

A feature of the combination of the generator in accordance with the invention and an electrode assembly having two adjacent electrodes is that the output is virtually bistable. When operating in desiccation mode, the entire electrode surface is in contact with an electrically conductive medium and therefore the load impedance is comparatively low, consequently inhibiting the rise in output voltage to a level sufficient for arcing. Conversely, when in cutting or tissue vaporisation mode, the entire active electrode surface is covered with a layer of vapour which is of much higher impedance, and the vapour pocket is sustained by arcing within it so that nearly all of the power dissipation occurs within the vapour envelope. In order to traverse from a desiccation mode to the cutting mode, a high power burst is required, hence the positioning of the power/load curve peak between the desiccation and cutting operation points on the curve. By allowing the output power to increase with impedance in this way, a high power burst of sufficient energy to create arcing is achieved despite the low impedance presented by the electrodes. As the supply voltage to the oscillator is increased, it has a greater propensity to flip into the cut mode, whilst at lower supply voltage levels, the bistable nature of the output, although more pronounced, tends towards the desiccation state.

The bistable properties arise not only from the electrode impedance behaviour, but also from the shape of the power/load impedance curve. The flatter the load curve, the more constant the output power across a band of impedances and the less pronounced the effect.

Referring to FIG. 9, it will be appreciated that in the cut or tissue vaporisation mode, a power equilibrium point is achieved by virtue of the decreasing output power as impedance increases. In the desiccation mode, the equilibrium is less straightforward, because there are two impedance change mechanisms. The first mechanism is the heating of the conductive medium and/or tissue which, due its positive coefficient of conductivity, results in a falling impedance initially, so that when power is first applied, the operating point moves towards the lefthand side of the diagram in FIG. 9. Consequently, there is a well-defined equilibrium point defined by the reduction in impedance with increasing power supply voltage, and the consequent reduction in delivered output power. However, when the saline medium or tissue fluids in contact with the active electrode start to boil, small water vapour bubbles begin to form which increase the impedance. When the generator is about to flip into the cutting mode, impedance rise due to steam formation is dominant. The impedance change therefore becomes positive with increasing supply voltage, and the operating point moves towards the righthand side of the diagram, which allows greater input power as a result of the shape of the load curve, causing a rapid change to cutting or vaporisation mode. As steam formation continues to increase, the increasing impedance causes a fall-off in delivered output power.

The applicants have found that the inherent equilibria described above may be insufficient to maintain a stable coagulation state or a stable cutting state. It is for this reason, that the RF output voltage from the RF oscillator 60 (FIG. 5) is limited, the limiting occurring extremely rapidly, typically with a response time of 20 $\mu$s or less. Excessive radio frequency interference is avoided by linear variation of the oscillator switching device "on" time in response to a feedback signal from the voltage threshold detector. This technique is used in conjunction with the RF oscillator having a comparatively low output Q when matched to the load, this Q being sufficient to suppress switching noise without inordinately damping the response to output voltage threshold detection.

Figure 10:
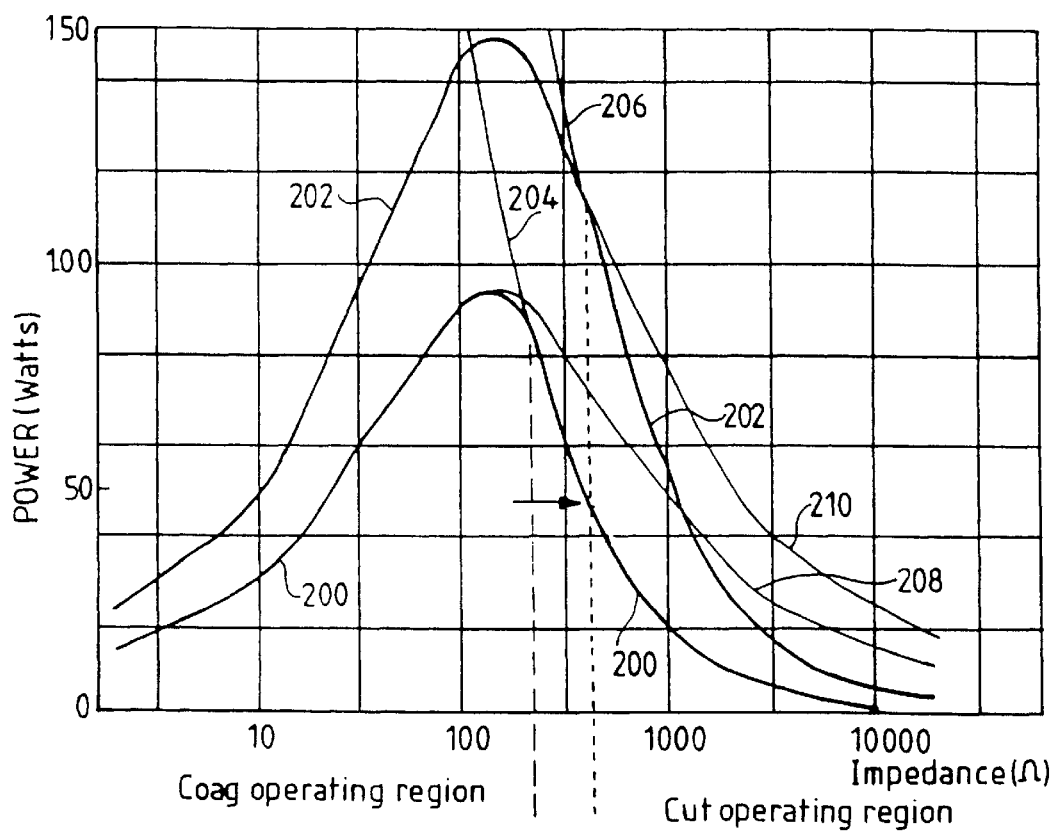
FIG. 10 is a graph showing the variation of output power for generator as a function of load impedance after modification of the generator characteristics in response to output voltage sensing.

By way of example, the effect of voltage threshold control for a particular electrode configuration is shown in FIG. 10, The heavy lines 200, 202 indicate the modified power/load impedance characteristics. For desiccation, shown by line 200, the switched mode power supply is set to produce a peak (matched) open loop output power of between 75 watts and 110 watts, with the actual peak power in this case being about 90 watts. For cutting and vaporisation (shown by line 202), the peak power can be between 120 watts and 175 watts. In this case it is 150 watts. As examples, the voltage thresholds are set at 180 volts peak for desiccation and 300 volts peak for cutting, as illustrated by the hyperbolic constant voltage lines 204 and 206 respectively. The power/impedance curves follow the respective constant voltage threshold lines to the right of their intersection with the unmodified open loop curves 208 and 210. Thus, it will be understood that the desiccation threshold line represents the maximum voltage that can be achieved in the desiccation mode before arcing is produced, whilst the cut threshold line limits the cutting or tissue vaporisation performance to achieve the desired tissue effect and, in the extreme, to avoid electrode burn-out. The desiccation threshold line also represents a voltage insufficient to achieve arcing for cutting or vaporising tissue.

A significant feature of the generator characteristic for electrosurgical cutting or tissue vaporisation is that at peak power (matched impedance) the load impedance lies between the impedances corresponding to the threshold voltages at that power level. In contrast, in the desiccation mode, the power/load impedance characteristic has a power peak at an impedance lying below the desiccation threshold line at that power level.

In practice, the output power in the desiccation mode will be higher than in the cutting or tissue vaporisation mode. The reason for this statement (despite the apparent contradiction with the load curves in FIG. 10) is that the equilibrium points described above lie at different points on the respective curves. To ensure cutting, the high peak power of the higher curve is required to reach the cut threshold line (corresponding to 300 volts peak). The cutting mode then follows the cutting or vaporisation threshold line. The cutting operating point is defined by the load impedance created when a suitable level of arcing is occurring. Typically, the load impedance in these circumstances is greater than 1000 ohms. Thus, although a full 150 watt peak power is available to ensure that vapour pockets are formed to promote arcing for cutting, the actual power drawn during cutting or tissue vaporisation for this particular electrode example may be between 30 watts and 40 watts. This situation is more easily understood if reference is also made to FIG. 3.

In the desiccation mode, the operating point is determined by the positive power coefficient of impedance arising from steam generation. Consequently, the equilibrium naturally occurs in the region of the peak of the desiccation mode power/load impedance curve.

Blended modes can be used by constantly alternating between desiccation and cut states or by altering the position of the thresholds.

The invention is useful for dissection, resection, vaporisation, desiccation and coagulation of tissue and such combinations of these functions with particular application in hysteroscopic, laparoscopic, colposcopic (including vaginal speculum) and open surgical procedures on the female genital tract and adnexal related diseases. Hysteroscopic operative procedures may include: removal of submucosal fibroids, polyps and malignant neoplasms; resection of congenital uterine anomalies such as a septum or subseptum; division of synechiae (adhesiolysis); ablation of diseased or hypertrophic endometrial tissue; and haemostasis. Laparoscopic operative procedures may include: removal of subserosal and pedunculated fibroids, ablation of ectopic endometrium, ovarian cystectomy and ovarian drilling procedures; oophorectomy, salpingo-oophorectomy, subtotal hysterectomy and laparoscopically assisted vaginal hysterectomy (LAVH) as may be performed for benign or malignant diseases laparoscopic uterosacral nerve ablation (LUNA); fallopian tube surgery as correction of ectopic pregnancy or complications arising from acquired obstructions; division of abdominal adhesions; and haemostasis.

The invention is also useful in the lower female genital tract, including treatment of the cervix, vagina and external genitalia whether accessed directly or using instrumentation comprising generally speculae and colposcopes. Such applications include: vaginal hysterectomy and other pelvic procedures utilising vaginal access: LLETZ/LEEP procedure (large loop excision of the transformation zone) or excision of the transformation zone of the endocervix; removal of cystic or septic lesions; ablation of genital or venereal warts; excision of benign and malignant lesions; cosmetic and surgical repairs including vaginal prolapse; excision of diseased tissue; and haemostasis.

The invention is also useful for dissection, resection, vaporisation, desiccation and coagulation of tissue and such combinations of these functions with particular application in arthroscopic surgery as it pertains to endoscopic and percutaneous procedures performed on joints of the body including but not limited to such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridgement as applies to any of the synovial joints of the body; including thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue; and haemostasis.

The invention is also useful for dissection, resection, vaporisation, desiccation and coagulation of tissue and such combinations of these functions with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURP) including but not limited to interstitial ablation of the prostate gland by a percutaneous or perurethral route whether performed for benign or malignant disease; transurethral or percutaneous resection of urinary tract tumours as they may arise as primary or secondary neoplasms and further as they may arise anywhere in the urological tract from the calyces of the kidney to the external urethral meatus; division of strictures as they may arise as the pelviureteric junction (PUJ), ureter, ureteral orifice, bladder neck or urethra, correction of ureterocoele; shrinkage of bladder diverticular; cystoplasty procedures as they pertain to corrections of voiding dysfunction; thermally induced shrinkage of pelvic floor as a corrective treatment for bladder neck descent; excision or diseased tissue; and haemostasis.

The invention is also useful for dissection, resection, vaporisation, desiccation and coagulation of tissue and such combinations of these functions with particular application in surgery on the ear, nose and throat (ENT) and more particularly procedures performed on the oropharynx, nasopharynx and sinuses. These procedures may be performed through the mouth or nose using speculae or gags or using endoscopic techniques such as functional endoscopic sinus surgery (FESS). Functional endoscopic sinus procedures may include: removal of chronically diseased inflamed and hypertrophic mucus linings, polyps and neoplasms from the various anatomical sinuses of the skull; excision of diseased tissue; and haemostasis. Procedures on the nasopharvnx may include: removal of chronically diseased inflamed and hypertrophic mucus linings, polyps and neoplasms from the turbinates and nasal passages; submucus resection of the nasal septum; excision of diseased tissue; and haemostsis. Procedures on the oropharynx may include: removal of chronically diseased inflamed and hypertrophic tissue, polyps and neoplasms particularly as they occur related to the tonsil, adenoid, epi- and supraglottic region, and salivary glands; as an alternative method to the procedure commonly known as laser assisted uvulopalatoplasty (LAUP); excision of diseased tissue; and haemostasis.

It is evident from the scope of applications of the invention that it has further additional applications for dissection, resection, vaporisation, desiccation and coagulation of tissue and such combinations of these functions in general laparoscopic, thoracoscopic and neurosurgical procedures being particularly useful in the removal of diseased tissue and neoplastic disease whether benign or malignant.

Surgical procedures using a system incorporating the generator of the present invention include introducing the electrode assembly to the surgical site whether through an artificial (cannula) or natural conduit, which may be in an anatomical body cavity or space such as the human uterus or one created surgically either using the invention or another technique. The cavity or space may be distended during the procedure using a fluid or may be naturally held open by anatomical structures. The surgical site may be bathed in a continuous flow of conductive fluid such as saline solution either to fill and distend the cavity or to create a locally irrigated environment around the tip of the electrode assembly in a gas filled cavity or on an external body surface or other such tissue surfaces exposed during part of a surgical procedure. The irrigating fluid may be aspirated from the surgical site to remove products created by application of the RF energy, tissue debris or blood. The procedures may include simultaneous viewing of the site via an endoscope or using indirect visualisation means.

What is claimed is:

1. A method of operating an electrosurgical system having at least a tissue desiccation mode and a tissue cutting or vaporisation mode, the system having a radio frequency power generator coupled to an electrode assembly having an electrode for operation in a conductive liquid, wherein the method comprises:

selecting one of the said modes;

when the desiccation mode is selected, automatically adjusting the radio frequency power supplied to the electrode assembly to maintain the conductive liquid adjacent the electrode at its boiling point for tissue desiccation without creating a vapour pocket surrounding the electrode; and when the cutting or vaporisation mode is selected, automatically adjusting the radio frequency power supplied to the electrode to maintain a vapour pocket surrounding the electrode.

2. A method according to claim 1, wherein, in the cutting or vaporisation mode, the radio frequency power supplied to the electrode is automatically limited to prevent overheating of the electrode.

3. A method according to claim 2, wherein the radio frequency power supplied to the electrode is automatically adjusted by limiting the output voltage applied to the electrode to predetermined first and second voltage values, the first voltage value being used in the desiccation mode, and the second voltage value, which is higher than the first voltage value, being used in the curting or vaporisation mode.

4. A method according to claim 3, wherein the first and second voltage values are in the ranges of from 150V to 200V and from 250V to 600V respectively, the voltages being peak voltages.

* * * * *